(12) United States Patent
Kaiser et al.

(10) Patent No.: US 8,231,654 B2
(45) Date of Patent: Jul. 31, 2012

(54) ADJUSTABLE KNOTLESS LOOPS

(75) Inventors: Ryan A. Kaiser, Leesburg, IN (US);
Gregory J. Denham, Warsaw, IN (US);
Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/102,182

(22) Filed: May 6, 2011

(65) Prior Publication Data

US 2011/0213416 A1  Sep. 1, 2011

Related U.S. Application Data

(60) Division of application No. 12/196,398, filed on Aug. 22, 2008, now Pat. No. 7,959,650, which is a continuation-in-part of application No. 11/541,506, filed on Sep. 29, 2006, now Pat. No. 7,601,165, and a continuation-in-part of application No. 11/935,681, filed on Nov. 6, 2007, now Pat. No. 7,905,903, and a continuation-in-part of application No. 11/784,821, filed on Apr. 10, 2007.

(51) Int. Cl.
*A61B 17/04* (2006.01)

(52) U.S. Cl. ....................................... 606/232

(58) Field of Classification Search ............... 606/74, 606/103, 223–225, 228; 52/22; 24/115 H; 604/103.04; 600/29–30, 37
See application file for complete search history.

(56) References Cited

U.S. PATENT DOCUMENTS

| 65,499 | A | 6/1867 | Miller |
|---|---|---|---|
| 126,366 | A | 4/1872 | Wills |
| 233,475 | A | 10/1880 | Cook et al. |
| 261,501 | A | 7/1882 | Vandermark |
| 268,407 | A | 11/1882 | Hughes |
| 417,805 | A | 12/1889 | Beaman |
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |

(Continued)

FOREIGN PATENT DOCUMENTS

AU  4957264  3/1966

(Continued)

OTHER PUBLICATIONS

US 6,238,418, 05/2001, Schwartz et al. (withdrawn).

(Continued)

*Primary Examiner* — Melanie Tyson
*Assistant Examiner* — Son Dang
(74) *Attorney, Agent, or Firm* — Harness, Dickey

(57) ABSTRACT

Methods of attaching a soft tissue to an adjacent bone at a defect site are provided. At least one adjustable loop of a flexible construct is passed through the soft tissue. The at least one adjustable loop is passed through a passage construct. A locking member is passed through the at least one adjustable loop and the adjustable loop is reduced about or within the locking member such that the at least one loop is frictionally retained in the passage construct and locked in place by the locking member to thereby secure the soft tissue.

25 Claims, 16 Drawing Sheets

U.S. PATENT DOCUMENTS

| | | |
|---|---|---|
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et at |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs, deceased et al. |
| 4,301,551 A | 11/1981 | Dore et al. |
| 4,312,337 A | 1/1982 | Donohue |
| 4,316,469 A | 2/1982 | Kapitanov et al. |

| | | | | | |
|---|---|---|---|---|---|
| 4,326,531 A | 4/1982 | Shimonaka et al. | 4,773,910 A | 9/1988 | Chen et al. |
| 4,345,601 A | 8/1982 | Fukuda | 4,775,380 A | 10/1988 | Seedhom et al. |
| 4,349,027 A | 9/1982 | DiFrancesco | 4,776,328 A | 10/1988 | Frey et al. |
| 4,388,921 A | 6/1983 | Sutter et al. | 4,781,190 A | 11/1988 | Lee et al. |
| 4,400,833 A | 8/1983 | Kurland | 4,784,126 A | 11/1988 | Hourahane et al. |
| 4,402,445 A | 9/1983 | Green | 4,787,882 A | 11/1988 | Claren et al. |
| 4,409,974 A | 10/1983 | Freedland | 4,790,297 A | 12/1988 | Luque et al. |
| 4,438,769 A | 3/1984 | Pratt et al. | 4,793,363 A | 12/1988 | Ausherman et al. |
| 4,441,489 A | 4/1984 | Evans et al. | 4,809,695 A | 3/1989 | Gwathmey et al. |
| 4,454,875 A | 6/1984 | Pratt et al. | 4,813,406 A | 3/1989 | Ogle, II |
| 4,462,395 A | 7/1984 | Johnson | 4,823,794 A | 4/1989 | Pierce |
| 4,463,753 A | 8/1984 | Gustilo | 4,828,562 A | 5/1989 | Kenna |
| 4,473,102 A | 9/1984 | Ohman et al. | 4,832,026 A | 5/1989 | Jones |
| 4,484,570 A | 11/1984 | Sutter et al. | 4,834,098 A | 5/1989 | Jones |
| 4,489,446 A | 12/1984 | Reed | 4,838,282 A | 6/1989 | Strasser et al. |
| 4,493,323 A | 1/1985 | Albright et al. | 4,841,960 A | 6/1989 | Garner |
| 4,496,468 A | 1/1985 | House et al. | 4,851,005 A | 7/1989 | Hunt et al. |
| 4,505,274 A | 3/1985 | Speelman | 4,858,608 A | 8/1989 | McQuilkin et al. |
| 4,509,516 A | 4/1985 | Richmond | 4,860,513 A | 8/1989 | Whitman |
| 4,531,522 A | 7/1985 | Bedi et al. | 4,863,383 A | 9/1989 | Grafelmann et al. |
| 4,532,926 A | 8/1985 | O'Holla | 4,870,957 A | 10/1989 | Goble et al. |
| 4,534,350 A | 8/1985 | Golden et al. | 4,873,976 A | 10/1989 | Schreiber |
| 4,535,764 A | 8/1985 | Ebert | 4,887,601 A | 12/1989 | Richards |
| 4,537,185 A | 8/1985 | Stednitz | 4,890,615 A | 1/1990 | Caspari et al. |
| 4,549,545 A | 10/1985 | Levy | 4,893,619 A | 1/1990 | Dale et al. |
| 4,549,652 A | 10/1985 | Free | 4,893,974 A | 1/1990 | Fischer et al. |
| 4,561,432 A | 12/1985 | Mazor | 4,895,148 A | 1/1990 | Bays et al. |
| 4,564,007 A | 1/1986 | Coombs et al. | 4,896,668 A | 1/1990 | Popoff et al. |
| 4,570,623 A | 2/1986 | Ellison et al. | 4,898,156 A | 2/1990 | Gatturna et al. |
| 4,573,844 A | 3/1986 | Smith | 4,899,743 A | 2/1990 | Nicholson et al. |
| 4,576,608 A | 3/1986 | Homsy | 4,901,721 A | 2/1990 | Hakki |
| 4,584,722 A | 4/1986 | Levy et al. | 4,923,461 A | 5/1990 | Caspari et al. |
| 4,590,928 A | 5/1986 | Hunt et al. | 4,927,421 A | 5/1990 | Goble et al. |
| 4,595,007 A | 6/1986 | Mericle | 4,946,468 A | 8/1990 | Li |
| 4,596,249 A | 6/1986 | Freda et al. | 4,950,270 A | 8/1990 | Bowman et al. |
| 4,602,635 A | 7/1986 | Mulhollan et al. | 4,950,285 A | 8/1990 | Wilk |
| 4,602,636 A | 7/1986 | Noiles | 4,960,381 A | 10/1990 | Niznick |
| 4,604,997 A | 8/1986 | De Bastiani et al. | 4,961,741 A | 10/1990 | Hayhurst |
| 4,605,414 A | 8/1986 | Czajka | 4,968,315 A | 11/1990 | Gatturna |
| 4,616,650 A | 10/1986 | Green et al. | 4,968,317 A | 11/1990 | Tormala et al. |
| 4,621,640 A | 11/1986 | Mulhollan et al. | 4,969,886 A | 11/1990 | Cziffer et al. |
| 4,624,254 A | 11/1986 | McGarry et al. | 4,976,736 A | 12/1990 | White et al. |
| 4,632,100 A | 12/1986 | Somers et al. | 4,978,350 A | 12/1990 | Wagenknecht et al. |
| 4,635,637 A | 1/1987 | Schreiber | 4,979,956 A | 12/1990 | Silvestrini |
| 4,636,121 A | 1/1987 | Miller | 4,983,176 A | 1/1991 | Cushman et al. |
| 4,641,652 A | 2/1987 | Hutterer et al. | 4,988,351 A | 1/1991 | Paulos et al. |
| 4,649,952 A | 3/1987 | Jobe | 4,994,074 A | 2/1991 | Bezwada et al. |
| 4,653,486 A | 3/1987 | Coker | 4,997,433 A | 3/1991 | Goble et al. |
| 4,653,487 A | 3/1987 | Maale | 5,002,550 A | 3/1991 | Li |
| 4,653,489 A | 3/1987 | Tronzo | 5,002,562 A | 3/1991 | Oberlander |
| 4,655,777 A | 4/1987 | Dunn et al. | 5,007,921 A | 4/1991 | Brown |
| 4,662,068 A | 5/1987 | Polonsky | 5,030,224 A | 7/1991 | Wright et al. |
| 4,667,662 A | 5/1987 | Titone et al. | 5,037,422 A | 8/1991 | Hayhurst et al. |
| 4,667,675 A | 5/1987 | Davis | 5,041,129 A | 8/1991 | Hayhurst et al. |
| 4,669,473 A | 6/1987 | Richards et al. | 5,046,513 A | 9/1991 | Gatturna et al. |
| 4,683,895 A | 8/1987 | Pohndorf | 5,047,030 A | 9/1991 | Draenert et al. |
| 4,688,561 A | 8/1987 | Reese | 5,053,046 A | 10/1991 | Janese |
| 4,690,169 A | 9/1987 | Jobe | 5,053,047 A | 10/1991 | Yoon |
| 4,696,300 A | 9/1987 | Anderson | 5,059,201 A | 10/1991 | Asnis |
| 4,705,040 A | 11/1987 | Mueller et al. | 5,059,206 A | 10/1991 | Winters |
| 4,708,132 A | 11/1987 | Silvestrini | 5,061,277 A | 10/1991 | Carpentier et al. |
| 4,714,475 A | 12/1987 | Grundei et al. | 5,062,344 A | 11/1991 | Gerker |
| 4,716,893 A | 1/1988 | Fischer et al. | 5,062,843 A | 11/1991 | Mahony, III |
| 4,719,671 A | 1/1988 | Ito et al. | 5,064,431 A | 11/1991 | Gilbertson et al. |
| 4,719,917 A | 1/1988 | Barrows et al. | 5,074,874 A * | 12/1991 | Yoon et al. .................. 606/224 |
| 4,723,540 A | 2/1988 | Gilmer, Jr. | 5,078,731 A | 1/1992 | Hayhurst |
| 4,724,839 A | 2/1988 | Bedi et al. | 5,078,843 A | 1/1992 | Pratt |
| 4,728,332 A | 3/1988 | Albrektsson | 5,084,050 A | 1/1992 | Draenert |
| 4,738,255 A | 4/1988 | Goble et al. | 5,084,058 A | 1/1992 | Li |
| 4,741,330 A | 5/1988 | Hayhurst | 5,085,661 A | 2/1992 | Moss |
| 4,741,336 A | 5/1988 | Failla et al. | 5,087,263 A | 2/1992 | Li |
| 4,744,353 A | 5/1988 | McFarland | 5,092,866 A | 3/1992 | Breard et al. |
| 4,744,793 A | 5/1988 | Parr et al. | 5,098,435 A | 3/1992 | Stednitz et al. |
| 4,750,492 A | 6/1988 | Jacobs | 5,100,415 A | 3/1992 | Hayhurst |
| 4,760,843 A | 8/1988 | Fischer et al. | 5,100,417 A | 3/1992 | Cerier et al. |
| 4,760,844 A | 8/1988 | Kyle | 5,116,337 A | 5/1992 | Johnson |
| 4,760,848 A | 8/1988 | Hasson | 5,116,373 A | 5/1992 | Jakob et al. |
| 4,772,261 A | 9/1988 | Von Hoff et al. | 5,116,375 A | 5/1992 | Hofmann |
| 4,772,286 A | 9/1988 | Goble et al. | 5,123,913 A | 6/1992 | Wilk et al. |

| | | | | | | |
|---|---|---|---|---|---|---|
| 5,123,914 A | 6/1992 | Cope | | 5,372,146 A | 12/1994 | Branch |
| 5,127,785 A | 7/1992 | Faucher et al. | | 5,372,604 A | 12/1994 | Trott |
| 5,129,901 A | 7/1992 | Decoste | | 5,372,821 A | 12/1994 | Badylak et al. |
| 5,129,902 A | 7/1992 | Goble et al. | | 5,374,268 A | 12/1994 | Sander |
| 5,129,904 A | 7/1992 | Illi | | 5,379,492 A | 1/1995 | Glesser |
| 5,129,906 A | 7/1992 | Ross et al. | | 5,383,878 A | 1/1995 | Roger et al. |
| 5,139,499 A | 8/1992 | Small et al. | | 5,383,904 A | 1/1995 | Totakura et al. |
| 5,139,520 A | 8/1992 | Rosenberg | | 5,391,171 A | 2/1995 | Schmieding |
| 5,143,498 A | 9/1992 | Whitman | | 5,391,176 A | 2/1995 | de la Torre |
| 5,147,362 A | 9/1992 | Goble | | 5,391,182 A | 2/1995 | Chin |
| 5,149,329 A | 9/1992 | Richardson | | 5,393,302 A | 2/1995 | Clark et al. |
| 5,152,790 A | 10/1992 | Rosenberg et al. | | RE34,871 E | 3/1995 | McGuire et al. |
| 5,154,189 A | 10/1992 | Oberlander | | 5,397,356 A | 3/1995 | Goble et al. |
| 5,156,616 A | 10/1992 | Meadows et al. | | 5,403,328 A | 4/1995 | Shallman |
| 5,163,960 A | 11/1992 | Bonutti | | 5,403,329 A | 4/1995 | Hinchcliffe |
| D331,626 S | 12/1992 | Hayhurst et al. | | 5,403,348 A | 4/1995 | Bonutti |
| 5,169,400 A | 12/1992 | Muhling et al. | | 5,405,359 A | 4/1995 | Pierce |
| 5,176,682 A | 1/1993 | Chow | | 5,417,691 A | 5/1995 | Hayhurst |
| 5,178,629 A | 1/1993 | Kammerer | | 5,417,712 A | 5/1995 | Whittaker et al. |
| 5,183,458 A | 2/1993 | Marx | | 5,423,819 A | 6/1995 | Small et al. |
| 5,192,282 A | 3/1993 | Draenert et al. | | 5,423,823 A | 6/1995 | Schmieding |
| 5,197,987 A | 3/1993 | Koch et al. | | 5,423,860 A | 6/1995 | Lizardi et al. |
| 5,203,784 A | 4/1993 | Ross et al. | | 5,425,733 A | 6/1995 | Schmieding |
| 5,203,787 A | 4/1993 | Noblitt et al. | | 5,425,766 A | 6/1995 | Bowald et al. |
| 5,207,679 A | 5/1993 | Li | | 5,433,751 A | 7/1995 | Christel et al. |
| 5,209,753 A | 5/1993 | Biedermann et al. | | 5,437,680 A | 8/1995 | Yoon |
| 5,209,805 A | 5/1993 | Spraggins | | 5,439,684 A | 8/1995 | Prewett et al. |
| 5,211,647 A | 5/1993 | Schmieding | | 5,441,508 A | 8/1995 | Gazielly et al. |
| 5,211,650 A | 5/1993 | Noda | | 5,443,468 A | 8/1995 | Johnson |
| 5,214,987 A | 6/1993 | Fenton, Sr. | | 5,443,482 A | 8/1995 | Stone et al. |
| 5,219,359 A | 6/1993 | McQuilkin et al. | | 5,443,483 A | 8/1995 | Kirsch et al. |
| 5,222,976 A | 6/1993 | Yoon | | 5,443,509 A | 8/1995 | Boucher et al. |
| 5,224,946 A | 7/1993 | Hayhurst et al. | | 5,445,833 A | 8/1995 | Badylak et al. |
| 5,230,699 A | 7/1993 | Grasinger | | 5,447,512 A | 9/1995 | Wilson et al. |
| 5,232,436 A | 8/1993 | Janevski | | 5,451,203 A | 9/1995 | Lamb |
| 5,234,435 A | 8/1993 | Seagrave, Jr. | | 5,454,811 A | 10/1995 | Huebner |
| 5,235,238 A | 8/1993 | Nomura et al. | | 5,456,685 A | 10/1995 | Huebner |
| 5,236,445 A | 8/1993 | Hayhurst et al. | | 5,456,722 A | 10/1995 | McLeod et al. |
| 5,236,461 A | 8/1993 | Forte | | 5,458,601 A | 10/1995 | Young, Jr. et al. |
| 5,242,447 A | 9/1993 | Borzone | | 5,458,604 A | 10/1995 | Schmieding |
| 5,246,441 A | 9/1993 | Ross et al. | | 5,462,560 A | 10/1995 | Stevens |
| 5,249,899 A | 10/1993 | Wilson | | 5,464,426 A | 11/1995 | Bonutti |
| 5,258,015 A | 11/1993 | Li et al. | | 5,464,427 A | 11/1995 | Curtis et al. |
| 5,258,016 A | 11/1993 | DiPoto et al. | | 5,464,440 A | 11/1995 | Johansson et al. |
| 5,258,040 A | 11/1993 | Bruchman et al. | | 5,466,237 A | 11/1995 | Byrd, III et al. |
| 5,268,001 A | 12/1993 | Nicholson et al. | | 5,467,786 A | 11/1995 | Allen et al. |
| 5,269,160 A | 12/1993 | Wood | | 5,470,334 A | 11/1995 | Ross et al. |
| 5,269,783 A | 12/1993 | Sander | | 5,470,337 A | 11/1995 | Moss |
| 5,269,809 A | 12/1993 | Hayhurst et al. | | 5,470,338 A | 11/1995 | Whitfield et al. |
| 5,281,422 A | 1/1994 | Badylak et al. | | 5,472,452 A | 12/1995 | Trott |
| 5,282,809 A | 2/1994 | Kammerer et al. | | 5,474,565 A | 12/1995 | Trott |
| 5,282,832 A | 2/1994 | Toso et al. | | 5,474,568 A | 12/1995 | Scott |
| 5,282,867 A | 2/1994 | Mikhail | | 5,474,572 A | 12/1995 | Hayhurst |
| 5,285,040 A | 2/1994 | Brandberg et al. | | 5,478,344 A | 12/1995 | Stone et al. |
| 5,290,217 A | 3/1994 | Campos | | 5,478,345 A | 12/1995 | Stone et al. |
| 5,306,301 A | 4/1994 | Graf et al. | | 5,480,403 A | 1/1996 | Lee et al. |
| 5,312,422 A | 5/1994 | Trott | | 5,480,406 A | 1/1996 | Nolan et al. |
| 5,312,438 A | 5/1994 | Johnson | | 5,484,442 A | 1/1996 | Melker et al. |
| 5,318,577 A | 6/1994 | Li | | 5,486,197 A | 1/1996 | Le et al. |
| 5,318,578 A | 6/1994 | Hasson | | 5,490,750 A | 2/1996 | Gundy |
| 5,320,115 A | 6/1994 | Kenna | | 5,496,331 A | 3/1996 | Xu et al. |
| 5,320,626 A | 6/1994 | Schmieding | | 5,496,348 A | 3/1996 | Bonutti |
| 5,320,633 A | 6/1994 | Allen et al. | | 5,500,000 A | 3/1996 | Feagin et al. |
| 5,324,308 A | 6/1994 | Pierce | | 5,505,736 A | 4/1996 | Reimels et al. |
| 5,334,204 A | 8/1994 | Clewett et al. | | 5,507,754 A | 4/1996 | Green et al. |
| 5,336,229 A | 8/1994 | Noda | | 5,520,691 A | 5/1996 | Branch |
| 5,336,231 A | 8/1994 | Adair | | 5,520,700 A | 5/1996 | Beyar et al. |
| 5,336,240 A | 8/1994 | Metzler et al. | | 5,520,702 A | 5/1996 | Sauer et al. |
| 5,342,369 A | 8/1994 | Harryman, II | | 5,522,817 A | 6/1996 | Sander et al. |
| 5,346,462 A | 9/1994 | Barber | | 5,522,820 A | 6/1996 | Caspari et al. |
| 5,354,298 A | 10/1994 | Lee et al. | | 5,522,844 A | 6/1996 | Johnson |
| 5,356,413 A | 10/1994 | Martins et al. | | 5,522,845 A | 6/1996 | Wenstrom, Jr. |
| 5,358,511 A | 10/1994 | Gatturna et al. | | 5,522,846 A | 6/1996 | Bonutti |
| 5,360,431 A | 11/1994 | Puno et al. | | 5,524,946 A | 6/1996 | Thompson |
| 5,362,294 A | 11/1994 | Seitzinger | | 5,527,321 A | 6/1996 | Hinchliffe |
| 5,364,400 A | 11/1994 | Rego, Jr. et al. | | 5,527,342 A | 6/1996 | Pietrzak et al. |
| 5,368,599 A | 11/1994 | Hirsch et al. | | 5,527,343 A | 6/1996 | Bonutti |
| 5,370,661 A | 12/1994 | Branch | | 5,534,012 A | 7/1996 | Bonutti |
| 5,370,662 A | 12/1994 | Stone et al. | | 5,540,718 A | 7/1996 | Bartlett |

| Patent No. | Date | Inventor(s) |
|---|---|---|
| 5,545,178 A | 8/1996 | Kensey et al. |
| 5,545,228 A | 8/1996 | Kambin |
| 5,549,613 A | 8/1996 | Goble et al. |
| 5,549,617 A | 8/1996 | Green et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,295 A * | 7/1997 | Yoon .................... 606/151 |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,695,497 A | 12/1997 | Stahelin et al. |
| 5,697,929 A | 12/1997 | Mellinger |
| 5,699,657 A * | 12/1997 | Paulson .................... 57/22 |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,725,549 A | 3/1998 | Lam |
| 5,725,556 A | 3/1998 | Moser et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,766,176 A | 6/1998 | Duncan |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,860,973 A | 1/1999 | Michelson |
| 5,868,740 A | 2/1999 | LeVeen et al. |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,267 A | 7/1999 | Bonutti et al. |

| Patent | Date | Name |
|---|---|---|
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |
| 5,968,047 A | 10/1999 | Reed |
| 5,976,125 A | 11/1999 | Graham |
| 5,976,127 A | 11/1999 | Lax |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,997,542 A | 12/1999 | Burke |
| 5,997,552 A | 12/1999 | Person et al. |
| 6,001,100 A | 12/1999 | Sherman et al. |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,053,916 A | 4/2000 | Moore |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,062,344 A | 5/2000 | Okabe et al. |
| 6,068,648 A | 5/2000 | Cole et al. |
| 6,074,403 A | 6/2000 | Nord |
| 6,077,277 A | 6/2000 | Mollenauer et al. |
| 6,077,292 A | 6/2000 | Bonutti |
| 6,086,591 A | 7/2000 | Bojarski |
| 6,086,592 A | 7/2000 | Rosenberg et al. |
| 6,086,608 A | 7/2000 | Ek et al. |
| 6,096,060 A | 8/2000 | Fitts et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,283,973 B1 | 9/2001 | Hubbard et al. |
| 6,283,996 B1 | 9/2001 | Chervitz et al. |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |

| | | |
|---|---|---|
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 | 11/2005 | Kumar |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,004,959 B2 | 2/2006 | Bonutti |
| 7,066,942 B2 | 6/2006 | Treace |
| 7,066,944 B2 | 6/2006 | Laufer et al. |
| 7,087,064 B1 | 8/2006 | Hyde |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,201,722 B2 | 4/2007 | Krueger |
| 7,255,675 B2 | 8/2007 | Gertner et al. |

| | | | |
|---|---|---|---|
| 7,261,716 B2 | 8/2007 | Strobel et al. | |
| 7,264,634 B2 | 9/2007 | Schmieding | |
| 7,285,124 B2 | 10/2007 | Foerster | |
| 7,303,577 B1 | 12/2007 | Dean | |
| 7,306,417 B2 | 12/2007 | Dorstewitz | |
| 7,326,222 B2 | 2/2008 | Dreyfuss et al. | |
| 7,390,329 B2 | 6/2008 | Westra et al. | |
| 7,390,332 B2 | 6/2008 | Selvitelli et al. | |
| 7,442,210 B2 | 10/2008 | Segal et al. | |
| 7,585,311 B2 | 9/2009 | Green et al. | |
| 7,601,165 B2 | 10/2009 | Stone | |
| 7,608,098 B1 | 10/2009 | Stone et al. | |
| 7,615,076 B2 | 11/2009 | Cauthen, III et al. | |
| 7,632,287 B2 | 12/2009 | Baker et al. | |
| 7,651,509 B2 | 1/2010 | Bojarski et al. | |
| 7,658,750 B2 | 2/2010 | Li | |
| 7,658,751 B2 | 2/2010 | Stone et al. | |
| 7,670,279 B2 | 3/2010 | Gertner | |
| 7,678,123 B2 | 3/2010 | Chanduszko | |
| 7,695,493 B2 | 4/2010 | Saadat et al. | |
| 7,736,379 B2 | 6/2010 | Ewers et al. | |
| 7,758,594 B2 | 7/2010 | Lamson et al. | |
| 7,776,041 B1 | 8/2010 | Walters | |
| 7,819,895 B2 | 10/2010 | Ginn et al. | |
| 7,875,058 B2 | 1/2011 | Holmes, Jr. | |
| 7,981,140 B2 | 7/2011 | Burkhart | |
| 8,062,334 B2 | 11/2011 | Green et al. | |
| 2001/0014825 A1 | 8/2001 | Burke et al. | |
| 2001/0037131 A1 | 11/2001 | Schmieding et al. | |
| 2001/0037153 A1 | 11/2001 | Rockwood et al. | |
| 2001/0041916 A1 | 11/2001 | Bonutti | |
| 2001/0041937 A1 | 11/2001 | Rieser et al. | |
| 2001/0041938 A1 | 11/2001 | Hein | |
| 2001/0044639 A1 | 11/2001 | Levinson | |
| 2001/0047206 A1 | 11/2001 | Sklar et al. | |
| 2001/0051816 A1 | 12/2001 | Enzerink et al. | |
| 2001/0053934 A1 | 12/2001 | Schmieding | |
| 2002/0001964 A1 | 1/2002 | Choi | |
| 2002/0004669 A1 | 1/2002 | Bartlett | |
| 2002/0007182 A1 | 1/2002 | Kim | |
| 2002/0010513 A1 | 1/2002 | Schmieding | |
| 2002/0013608 A1 | 1/2002 | ElAttrache et al. | |
| 2002/0019649 A1 | 2/2002 | Sikora et al. | |
| 2002/0055780 A1 | 5/2002 | Sklar | |
| 2002/0058966 A1 | 5/2002 | Tormala et al. | |
| 2002/0099411 A1 | 7/2002 | Bartlett | |
| 2002/0111653 A1 | 8/2002 | Foerster | |
| 2002/0120270 A1 | 8/2002 | Trieu et al. | |
| 2002/0120292 A1 | 8/2002 | Morgan | |
| 2002/0123752 A1 | 9/2002 | Schultheiss et al. | |
| 2002/0128684 A1 | 9/2002 | Foerster | |
| 2002/0147463 A1 | 10/2002 | Martinek | |
| 2002/0161401 A1 | 10/2002 | Steiner | |
| 2002/0161439 A1 | 10/2002 | Strobel et al. | |
| 2002/0169452 A1 | 11/2002 | Tormala et al. | |
| 2002/0169477 A1 | 11/2002 | Demopulos et al. | |
| 2002/0169478 A1 | 11/2002 | Schwartz et al. | |
| 2002/0173788 A1 | 11/2002 | Bojarski et al. | |
| 2002/0188298 A1 | 12/2002 | Chan | |
| 2002/0193830 A1 | 12/2002 | Bonutti | |
| 2003/0023268 A1 | 1/2003 | Lizardi | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0065391 A1 | 4/2003 | Re et al. | |
| 2003/0078603 A1 | 4/2003 | Schaller et al. | |
| 2003/0078617 A1 | 4/2003 | Schwartz et al. | |
| 2003/0083662 A1 | 5/2003 | Middleton | |
| 2003/0088251 A1 | 5/2003 | Braun et al. | |
| 2003/0088272 A1 | 5/2003 | Smith | |
| 2003/0105477 A1 | 6/2003 | Schwartz et al. | |
| 2003/0105489 A1 | 6/2003 | Eichhorn et al. | |
| 2003/0120309 A1 | 6/2003 | Colleran et al. | |
| 2003/0130694 A1 | 7/2003 | Bojarski et al. | |
| 2003/0135214 A1 | 7/2003 | Fetto et al. | |
| 2003/0135239 A1 | 7/2003 | Gabriel et al. | |
| 2003/0135963 A1 | 7/2003 | Holbrook et al. | |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0044391 A1 | 3/2004 | Porter |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0251208 A1 | 11/2005 | Elmer et al. |
| 2005/0267479 A1 | 12/2005 | Morgan et al. |
| 2005/0267533 A1 | 12/2005 | Gertner |

| Publication No. | Date | Inventor |
|---|---|---|
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0100627 A1 | 5/2006 | Stone et al. |
| 2006/0116685 A1 | 6/2006 | Urbanski et al. |
| 2006/0121084 A1 | 6/2006 | Borden et al. |
| 2006/0135958 A1 | 6/2006 | Marissen et al. |
| 2006/0149266 A1 | 7/2006 | Cordasco |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0253130 A1 | 11/2006 | Wolniewicz |
| 2006/0271192 A1 | 11/2006 | Olsen et al. |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1* | 12/2006 | Bojarski et al. ............... 606/232 |
| 2007/0005080 A1 | 1/2007 | Wolniewicz et al. |
| 2007/0016305 A1 | 1/2007 | Chudik |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0142838 A1 | 6/2007 | Jordan |
| 2007/0185532 A1 | 8/2007 | Stone et al. |
| 2007/0191849 A1 | 8/2007 | ElAttrache et al. |
| 2007/0219558 A1 | 9/2007 | Deutsch |
| 2007/0239209 A1 | 10/2007 | Fallman |
| 2007/0239275 A1 | 10/2007 | Willobee |
| 2007/0250163 A1 | 10/2007 | Cassani |
| 2008/0027446 A1 | 1/2008 | Stone et al. |
| 2008/0046009 A1 | 2/2008 | Albertorio et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132753 A1 | 6/2008 | Goddard |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0188936 A1 | 8/2008 | Ball et al. |
| 2008/0221527 A1 | 9/2008 | Bradley et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0054928 A1 | 2/2009 | Denham et al. |
| 2009/0062854 A1 | 3/2009 | Kaiser et al. |
| 2009/0082805 A1 | 3/2009 | Kaiser et al. |
| 2009/0138002 A1 | 5/2009 | Fenton |
| 2009/0156997 A1 | 6/2009 | Trenhaile |
| 2009/0177233 A1 | 7/2009 | Malek |
| 2009/0192468 A1 | 7/2009 | Stone |
| 2009/0204146 A1 | 8/2009 | Kaiser et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0218625 A1 | 9/2011 | Berelsman et al. |
| 2011/0270278 A1 | 11/2011 | Overes et al. |

FOREIGN PATENT DOCUMENTS

| | | |
|---|---|---|
| AU | 440266 | 10/1967 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |

| | | |
|---|---|---|
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-05104992 A1 | 11/2005 |

OTHER PUBLICATIONS

"AperFix® System Surgical Technique Guide. Single Tunnel Double Bundle.™" Cayenne Medical brochure. (Aug. 2008) 8 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™0 Soft Anchor. It's Small. It's strong. And it's all suture . . ." Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-JOURNAL 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library, Printed May 19, 2005.
F. Alan Barber, M.D., "Using Sutures and Anchors," San Diego Shoulder Arthroscopy Course, 17th Annual Meeting, (Dec. 1, 2006).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct.), 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.

* cited by examiner

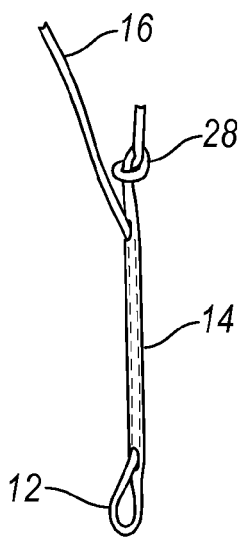 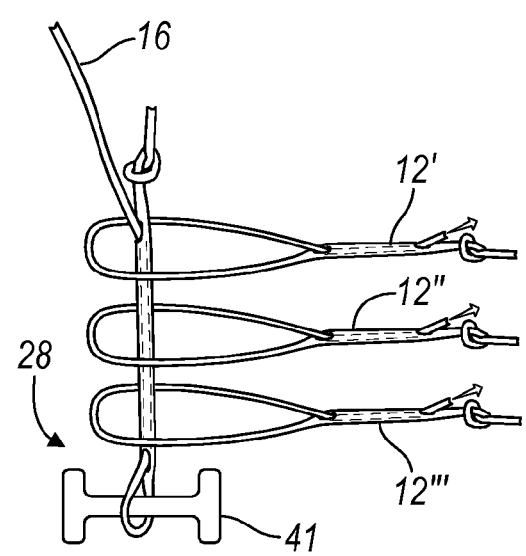
FIG. 12A  FIG. 12B
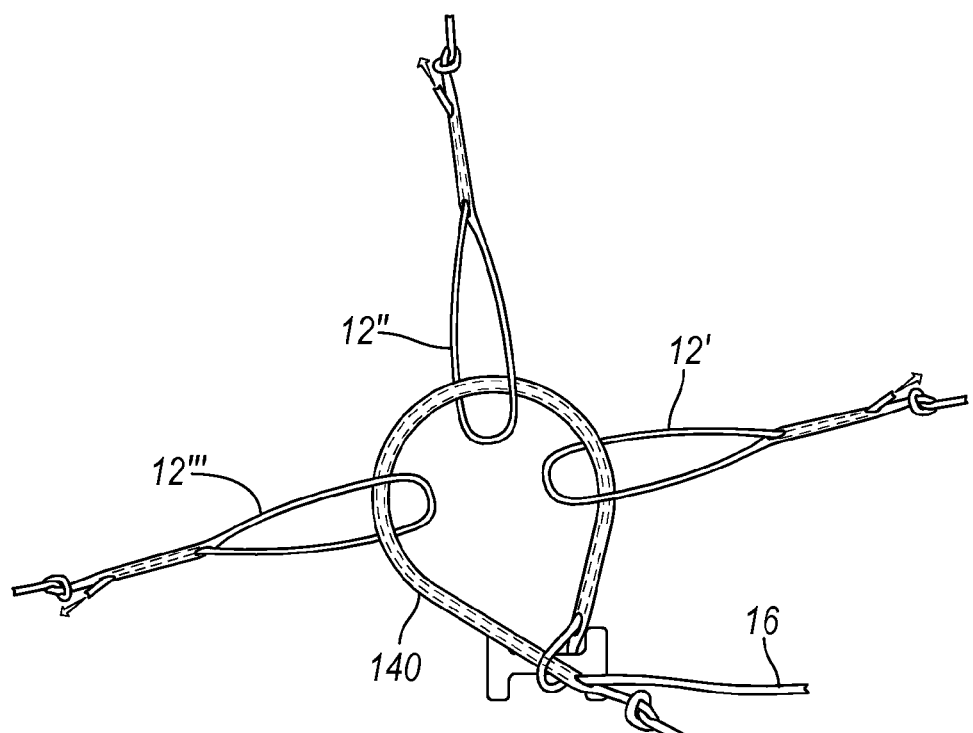
FIG. 12C

ADJUSTABLE KNOTLESS LOOPS

CROSS-RELATED APPLICATIONS

This application is a divisional of U.S. Application Ser. No. 12/196,398 filed on Aug. 22, 2008, which is a continuation-in-part of (a.) U.S. application Ser. No. 11/541,506 filed on Sep. 29, 2006, now U.S. Pat. No. 7,601,165 issued on Oct. 13, 2009; (b.) U.S. application Ser. No. 11/935,681 filed on Nov. 6, 2007, now U.S. Pat. No. 7,905,903 issued on Mar. 15, 2011; and (c.) to U.S. application Ser. No. 11/784,821 filed on Apr. 10, 2007. The aforementioned references are expressly incorporated herein in their entirety.

FIELD

The present disclosure relates to methods and apparatuses for securing a flexible construct. In particular, the present disclosure relates to securing a flexible construct with an adjustable loop.

BACKGROUND

The statements in this section merely provide background information related to the present disclosure and may not constitute prior art.

Surgical procedures are often performed on a body, for example, a human body or anatomy, to repair or replace various portions thereof. For example, the soft tissues of the body may need to be reattached to bones due to trauma, overuse, surgical intervention, or disease.

Soft tissues can be reattached to bone using fastening devices such as screws, staples, and various types of suture anchors. Soft tissues are often fixed to various positions on the bone. For example, to replace a natural tendon fixation point or to replace the tendon itself, fixing a graft to a selected bone area may be desired. One means to fix a soft tissue to the selected area is to provide a suture through a selected portion of the soft tissue and fix the other end of the suture to a selected area on the bone with the fastener. To secure the sutures, the free ends of the suture are tied together to form a knot.

The use of knots in surgical procedures, however, can be improved upon. In minimally invasive procedures, such as arthroscopic or laparoscopic procedures, the surgical site is not readily accessible and limits the surgeon's ability to tie a knot manually. One remote method of securing the suture is tying each of the suture ends into a knot extracorporeally and then remotely advancing the knot into the surgical site using suitably configured instruments. Securing the suture remotely can be cumbersome and time-consuming.

Accordingly, there is a need for improved devices for securing a suture without a knot. There is a need for surgical methods to facilitate easy and efficient securing of the suture.

SUMMARY

The present teachings provide methods of attaching a first tissue to a second tissue. At least one adjustable loop of a flexible construct is passed through at least the first soft tissue. The at least one adjustable loop is passed through a passage construct. A locking member is passed through the at least one adjustable loop and the adjustable loop is reduced about or within the locking member such that the at least one loop is frictionally retained in the passage construct and locked in place by the locking member to thereby secure at least the first tissue.

The present teachings also provide methods of attaching a first tissue to a second tissue. An adjustable loop is disposed through a bore defined by a fastener. A restriction element of the adjustable loop is secured on a receiving surface of the fastener. The adjustable loop is passed through the soft tissue. The fastener is fixed to an area adjacent the defect such that the adjustable loop and a proximal end of the fastener face the defect. The adjustable loop is then reduced in size to reduce the distance between the anchor and the first tissue.

The present teachings still further provide methods of attaching a first tissue to a second tissue. A first adjustable loop of a first flexible construct contained in a bore defined by a first fastener is passed through at least the first. A second adjustable loop of a second flexible construct contained in a bore defined by a second fastener is passed through the second tissue. The second fastener is attached to the first. The first adjustable loop and the second adjustable loop are passed through a passage construct. A locking member is passed through the two adjustable loops. The first and second adjustable loops are reduced within or about the locking member to thereby attach the first tissue and the second tissue.

The present teachings still further provide methods of attaching a rotator cuff to a bone at a site in need of repair. A first adjustable loop of a first flexible construct contained in a bore defined by a first fastener is passed through the rotator cuff. The first fastener is attached to the bone. A second adjustable loop of a second flexible construct contained in a bore defined by a second fastener is passed through the rotator cuff. The second fastener is attached to the bone at a first position with respect to the first fastener. The adjustable loops are passed over a self-contained locking member and subsequently reduced about the locking member.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 12A through 12C depict a plate type anchor according to various embodiments;

DETAILED DESCRIPTION

Figure 1:
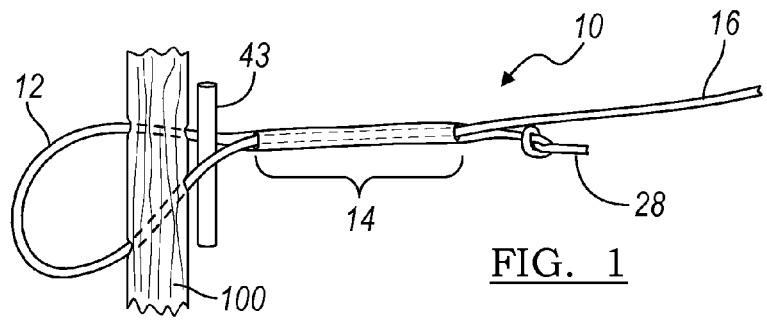
FIG. 1 depicts a flexible construct according to various embodiments.

The following description is merely exemplary in nature and is not intended to limit the present disclosure, application, or uses.

Referring to FIGS. 1-14C, the present teachings provide various surgical methods for connecting a first tissue 100 to a second tissue 200. The first tissue 100 and the second tissue 200 can be independently selected from bone or soft tissue to provide any of a bone-to-bone, a soft tissue-to-bone, or a soft tissue-to-soft tissue connection. The various components used in the surgical methods are presented first and then followed by illustrations of the surgical methods.

Referring to FIGS. 1 through 3B, the flexible construct 10 includes an adjustable loop 12 (or single loop), a passage 14, and an adjusting arm 16. Reduction of the adjustable loop 12 compresses the tissue and provides fixation of the tissue. The adjustable loop 12 and the surgical methods detailed herein, eliminate the need to tie a knot and thereby increase surgical efficiency. As compared to traditional sutures secured by tying a knot, the flexible construct 10 of various embodiments provides increased load to failure, has multiple-fold increased strength, has a decreased stretch at failure, and has multiple-fold stiffness at failure.

Figure 2:
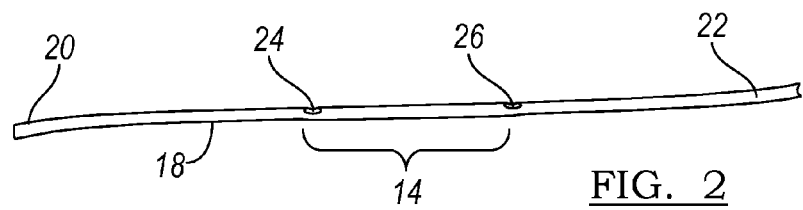
FIG. 2 depicts a fully extended flexible construct according to various embodiments.

Referring to FIG. 2, the flexible construct 10 can be made from any biocompatible material that is flexible and can pass through and secure a tissue. Exemplary materials include, but are not limited to, non-resorbable polymers, such as polyethylene or polyester, resorbable polymers, metals, and various combinations thereof. The materials can include those formed into a monofilament, multiple filaments, cables, and the like. In various embodiments, the flexible construct 10 is made of a hollow material to allow for the appropriate folding and tensioning thereon.

In various embodiments, the flexible construct 10 can be a suture 18. The suture 18 used to form the construct is generally a hollow suture having a distal end 20 and proximal end 22. The suture 18 can be formed as a braided or multiple-filament suture structure that is formed to define a substantially tubular hollow-shaped flexible construct 10.

The suture 18 contains a first opening 24 located closer to the distal end 20 and the second opening 26 located closer to the proximal end 22. In various embodiments, the first opening 24 and the second opening 26 can extend along a top surface of the suture 18 and are sized to accommodate passage of the distal end 20 of the suture therethrough. It is understood that the first opening 24 and the second opening 26 need not be formed by cutting the suture 18 or by removing any suture material. For example, the first opening 24 or the second opening 26 can be formed by passing the suture distal end 20 through the sidewall of the hollow tubular suture 18.

The passage 14 is defined by the area between the first opening 24 and the second opening 26. The passage 14 can be a short passage, can extend to the length of a fastener used therewith, or have a greater length, as further detailed later herein.

To provide the adjustable loop 12 and the adjusting arm 16, the distal end 20 of the suture 18 is passed through the first opening 24, into and through the passage 14, and advanced out of the second opening 26. The portion exiting from the second opening 26 provides the adjusting arm 16 and the folded end provides the adjustable loop 12.

Figure 3A:
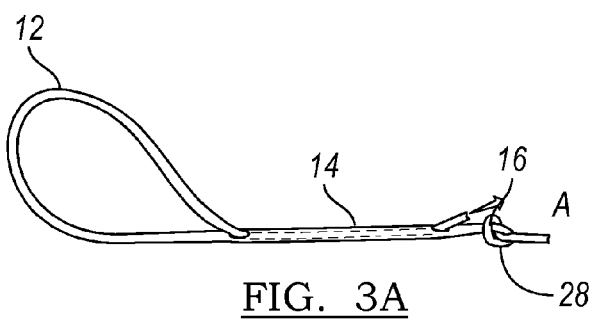
FIGS. 3A and 3B depict movement of the adjustable loop according to various embodiments.
Figure 3B:
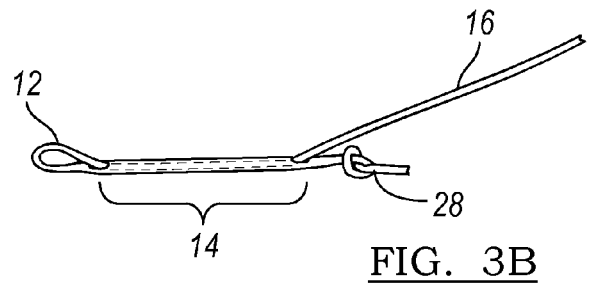

Referring to FIGS. 3A and 3B, the adjusting arm 16 is engaged or pulled in direction A to cause movement of the adjustable loop 12. As the adjustable loop 12 is reduced in size (or creating a smaller diameter loop 12), the adjusting arm 16 lengthens, as shown in FIG. 3B. In various embodiments, the movement of the suture 18 is only in the direction of arrow A and movement is prevented in the opposite direction. This unidirectional movement is controlled by maintaining tension (by pulling, for example) on the flexible construct 10 to radially compress the passage 14 about the suture portion contained therein as further detailed later herein.

To facilitate the unidirectional movement, a restriction element 28 can be included near the proximal end 22. The restriction element 28 controls movement of the adjustable loop 12 and the adjusting arm 16. Moreover, the restriction element 28 can prevent displacement of the flexible construct 10 in minimally invasive procedures. As depicted, the restriction element 28 is a knot. It is understood that the restriction element 28 does not provide the tissue fixation, but it is the tissue compression provided by the reduction of the adjustable loop 12 about the tissue that provides the fixation. The restriction element 28 can include other devices used to retain a suture, such as a suture clip.

Figure 4:
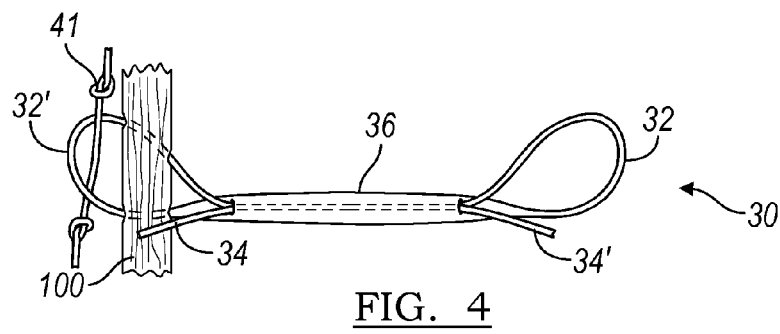
FIG. 4 depicts a flexible construct comprising two adjustable loops according to various embodiments.

Referring to FIG. 4, in further embodiments, a flexible construct 30 provides two adjustable loops 32 and 32' (or a double loop) on a single construct. Similar to the single adjustable loop of flexible construct 10 as detailed above, the adjustable loops 32 and 32' are reduced by engaging the respective adjusting arms 34 and 34'. For example, upon engaging the adjusting arm 34, the length of the flexible member forming the adjustable loop 32 is reduced as the material is passed through the passage 36. The movement of the adjusting arms 34 and 34' and thus the reduction of the adjustable loops 32 and 32' occur independently. Movement of the adjusting arms 34, 34' and the subsequent reduction of the adjustable loop 32, 32' size are generally unidirectional due to friction of the construct components within the passage 36. A further discussion of the various loops that are useful with the present teachings are disclosed in U.S. patent application Ser. No. 11/541,506 to Stone, filed Sep. 29, 2006 and U.S. patent application Ser. No. 11/784,821 to Kaiser et al. filed Apr. 10, 2007, and assigned to Biomet Sports Medicine, Inc., which are both incorporated by reference.

Figure 5A:
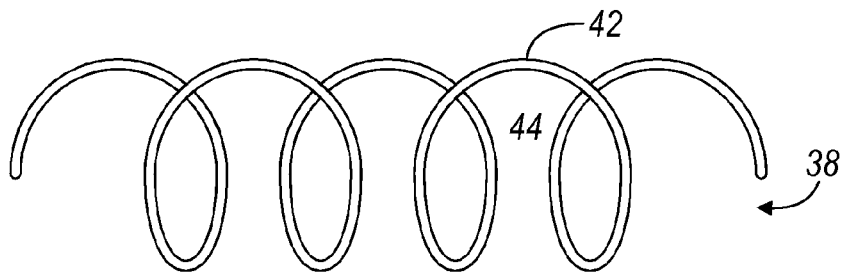
FIGS. 5A-5B depict various pathway constructs according to various embodiments.
Figure 5B:
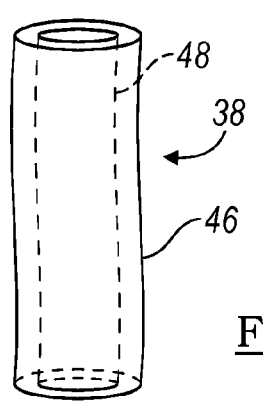

Referring to FIGS. 5A and 5B, a pathway construct 38 provides a passage that is used to guide, contain, or otherwise engage the flexible constructs 10 or 30. In various embodiments, the flexible constructs 10, 30 can be disposed about an exterior of the pathway construct 38. As will be detailed further in the discussion of FIGS. 7A-7D and 8A-9C, the pathway construct 38 can be created from another component in the system. The pathway constructs 38 are used to guide the flexible member construct 10 or 30 and can serve to keep the adjustable loop 12 in proper orientation during the surgical procedures.

Figure 6A:
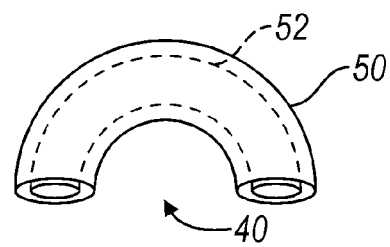
FIGS. 6A-6D depict various locking members according to various embodiments.
Figure 6B:
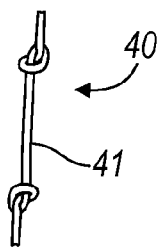
Figure 6C:
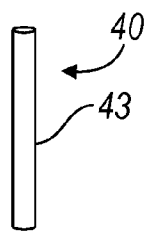
Figure 6D:
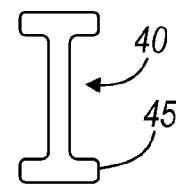

Turning to FIGS. 6A-6D, and as is illustrated in FIGS. 1 and 4, a locking member 40 is provided in the loops 12 or 32, 32' of the flexible members 10 or 30 respectively. In various embodiments, the locking member 40 can be an integral part of the adjustable loop 12 or another portion of the flexible construct, or the locking member 40 can be a separate piece, such as the use of the restriction element 28 as a locking member depicted in FIG. 7D. As shown in FIG. 6A, the locking member 40 can be an elbow 50 which defines a through passage 52 to receive a region of a suture 51, for example. In other embodiments, the locking member 40 can be a construct 41 made of a length of a flexible material having two knots located at the ends thereof as shown in FIGS. 4 and 6B, a tubular member 43 as shown in FIGS. 1 and 6C, or an I-shaped or dumbbell shaped member 45 as shown in FIG. 6D.

The locking member 40 secures and/or prevents the adjustable loops 12 or 32, 32' of the flexible members 10 or 30, respectively from being pulled back out of the tissue. The locking member 40 allows the adjustable loop portion 12 or 32 of the flexible construct 10 or 30, respectively, to rotate or slide so that the adjustable loop 12 does not "catch" on the locking member 40 prior to achieving the desired end size reduction or compression. The locking member 40 functions to prevent the adjustable loops 12 or 32, 32' from pulling out of the tissue, to prevent the adjustable loops 12 or 32, 32' from pulling out of the pathway construct, to tighten and/or securing of the tissue, and combinations thereof.

The flexible constructs 10 and 30 are useful in the various methods disclosed herein. The flexible constructs 10 and 30 and surgical techniques detailed herein can be used with various repairs of the shoulder, wrist, hand, ankle, foot, elbow, knee, or hip as non-limiting examples. The embodiments detailed herein are particularly useful in repairing certain soft tissue defects, for example, a labral tear. Exemplary repairs include Bankart Repair, SLAP Repair, Acromioclavicular separation, rotator cuff repair, capsule repair or capsulolabral reconstruction, biceps tenodesis, or deltoid repair of the shoulder; scapholunate ligament reconstruction or ulnar radial collateral ligament reconstruction of the wrist or hand; lateral stabilization, medial stabilization, Achilles tendon repair and reconstruction, halux valgus reconstruction, midfoot reconstruction, and forefoot reconstruction of the ankle or foot; lateral epicondylitis (tennis elbow) repair, ulnar or radial collateral ligament reconstruction, and biceps tendon reconstruction of the elbow; and extra-capsular repair, medial collateral ligament repair, lateral collateral ligament repair, posterior oblique ligament repair, joint capsule closure, iliotibial band tenodesis reconstruction, patellar realignment and repair, patellar ligament and tendon repair, and vastus medialis obliquus muscle advancement. It is understood that the techniques detailed herein can be used for orthopedic repair including cartilage repair, ligament repair, or tendon repair. The repair can be with an articular orthopedic surface or a non-articular and/or non-orthopedic surface.

Although an illustration of a particular embodiment may include a depiction of only the single loop flexible construct 10 or the double loop flexible construct 30, the embodiments and teachings herein are not so limited. It is understood that the preparation of the various constructs and assemblies detailed herein can be performed extra corporeally or at/within the surgical site. The various surgical methods allow tissue fixation without requiring the surgeon to tie knots in the flexible members.

Figure 7A:
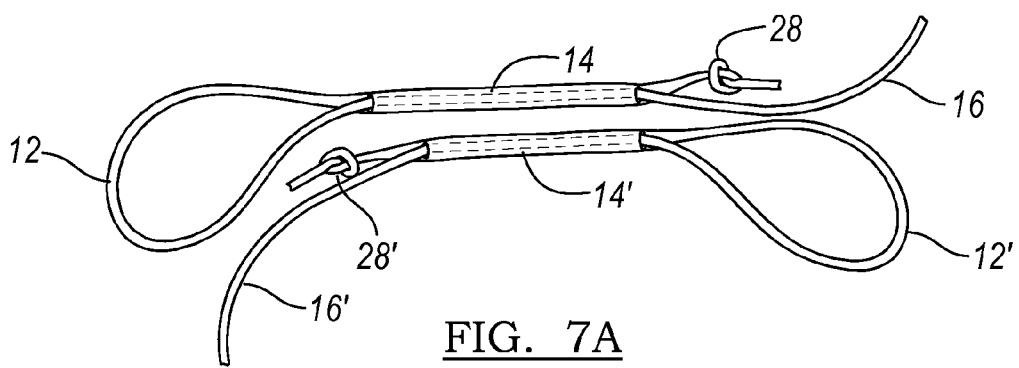
FIGS. 7A-7D depict a system employing a coiled flexible member pathway construct according to various embodiments.
Figure 7B:
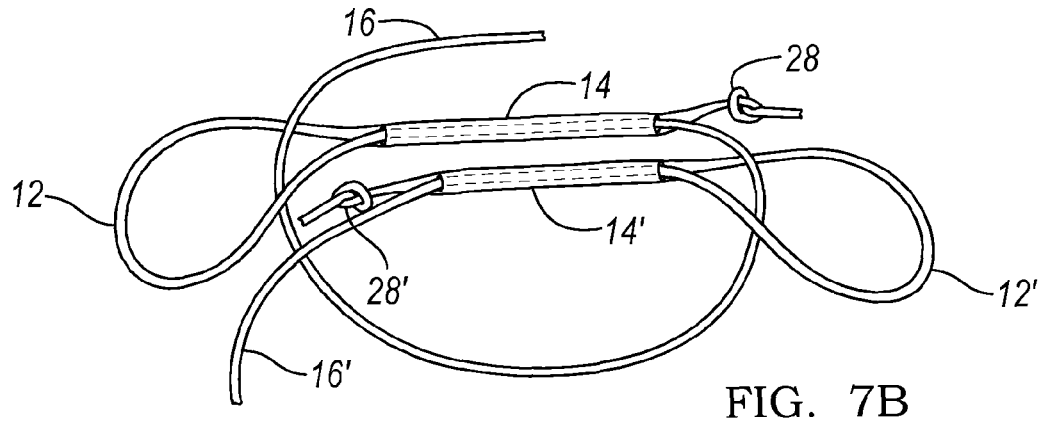
Figure 7C:
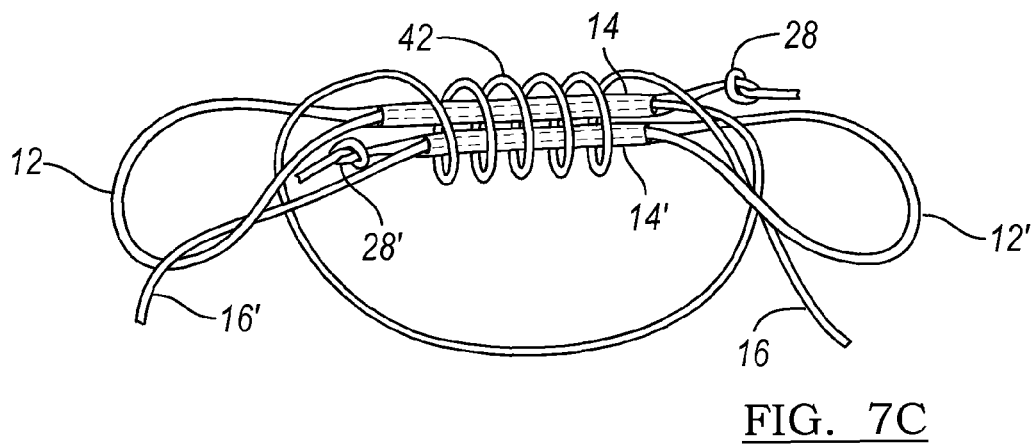

FIGS. 7A-7D depict a first surgical method according to the present teachings. Two flexible member constructs 10 and 10' are aligned such that the passages 14 are immediately adjacent as shown in FIG. 7A. Next, the adjustable loop 12 or a region of the passage 36 is passed through the interior or about an exterior of a pathway construct 38 shown as coil 42. The coil 42 is formed by wrapping a length of the adjusting arm 16 about a region of the adjustable loop 12, such as the passage 14. This wrapped system is similar to the coil preparation and flexible member securing referred to as a "Duncan loop" 42 to fishing hobbyist. Engaging or pulling the adjusting arm 16 which forms part of the Duncan loop causes the coil 42 to reduce about each respective passage 14 and 14' of the adjustable loops 12 and 12'.

Figure 7D:
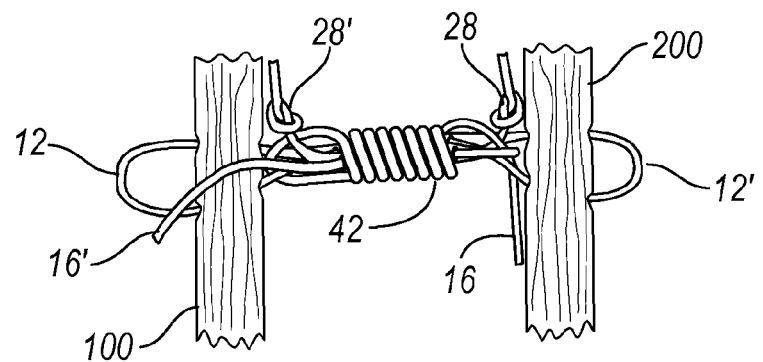

The securing elements 28 and 28' of each adjustable loop 12 and 12', respectively, are then passed through the opposing adjustable loop. As shown in FIG. 7D, the securing element 28 is passed through the adjustable loop of 12' and the securing element 28' is passed through the adjustable loop 12. The securing elements 28 and 28' serve as the locking member 40 for the opposing adjustable loop.

Next, the adjustable loop 12 is passed through the first tissue 100 and a second adjustable loop 12' is passed through the second tissue 200. Where a soft tissue is used, the adjustable loop 12 can be passed through the soft tissue by piercing a hole in the tissue prior to passing the adjustable loop 12 therethrough. This can be performed with a separate needle, a needle that is removably attached to the adjustable loop 12 or, in embodiments using a separate fastener, such as those illustrated later herein, with a tip of the fastener. Any suitable suture passer or other device can also be used to pass the adjustable loop 12 through the tissue such as those known in the art as "bird beak" passers or suture lariats. Two devices useful for passing the suture include those sold under the tradenames SpeedPass and ArthroPass, both made by Biomet Sports Medicine, Inc. of Warsaw, Ind. In embodiments where a hard tissue such as bone is one of the tissues 100 or 200, a bore can be placed in the bone to receive the adjustable loop 12 or a region of the flexible member construct 10. As shown in FIGS. 7A and 7D, the adjustable loop region 12 passes through the tissue 100 or 200 and a loop end 13 extends out of the tissue 100 or 200.

After the adjustable loops 12 and 12' are passed through the tissue and the restriction elements 28 and 28' are arranged to facilitate the tissue and adjustable loop securing, adjusting arms 16 and 16' are engaged. This causes the coil 42 and the adjustable loops to be reduced in size, as shown in the transition from FIG. 7C to FIG. 7D. The securing elements 28 and 28' serving as the locking members 40 prevent the adjustable loops 12 and 12' from passing back out of the tissue, and serve to increase the securing of the adjustable loops 12 and 12' at the tissue. The first tissue 100 and the second tissue 200 are brought in close proximity to effectuate securing. It is understood that the first tissue 100 and the second tissue 200 need not be discrete portions of tissue, but can be regions of the same area, for example, a partially torn rotator cuff.

Referring to the second embodiment of this group, as shown in FIGS. 5B, 8A-8D, 9A-9C, a tubular flexible member 46 defines the pathway construct 38 and the locking member 40. The tubular flexible member 46 can be a suture or any suitable flexible material, such as those listed above herein, which is sufficiently wide to accommodate the adjustable loops 12 or the adjustable loops 32 and 32'. In various embodiments, the tubular flexible member 46 can be a #2-0 to a #2 suture.

Specifically turning to FIGS. 8A-8D, the tubular flexible member 46 includes end openings 54 and 54' at each end thereof. To prepare the tubular flexible member 46, the tubular flexible member 46 is folded in half, and flexible construct receiving openings 56 and 56' are prepared therein. The flexible construct receiving openings 56 and 56' can be prepared by spreading a region of a braided suture material or by cutting a region of the tubular flexible member 46, for example, with a suture threader 58. The flexible construct receiving openings 56 and 56' are generally aligned with the end openings 54 and 54', respectively to define the pathway construct 38.

After defining the pathway construct between the openings 54 and 56 and 54' and 56', respectively, adjustable loops 12 and 12' are passed through eyes 60 and 60' of the suture threader 58. The adjustable loops 12 and 12' can be passed by hand or using a guide wire. The suture threader 58 loaded with the adjustable loops 12 and 12' is then advanced axially downwardly through the arms of the tubular flexible member 46 such that the adjustable loops 12 and 12' extend out of the openings 56 and 56'.

Figure 8A:
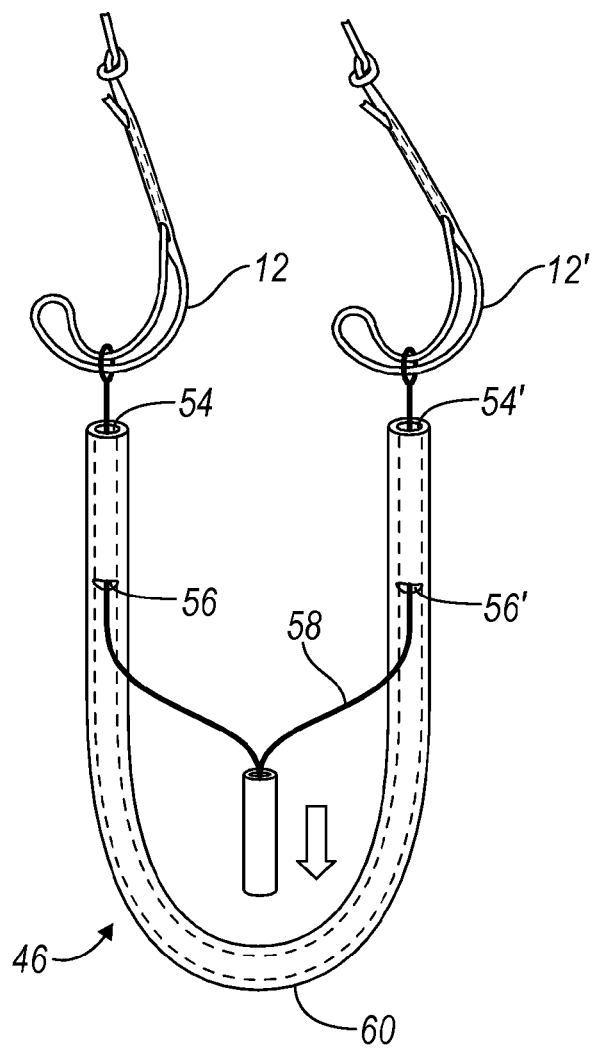
FIGS. 8A-8D depict a tubular flexible member pathway construct according to various embodiments.
Figure 8B:
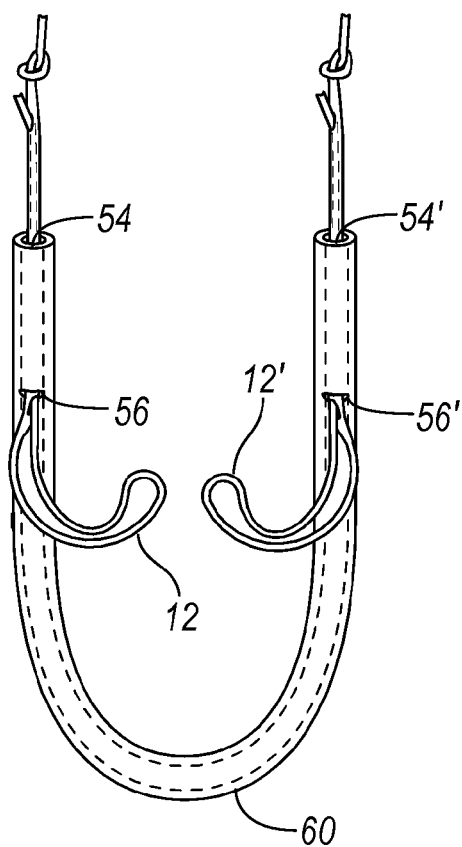
Figure 8C:
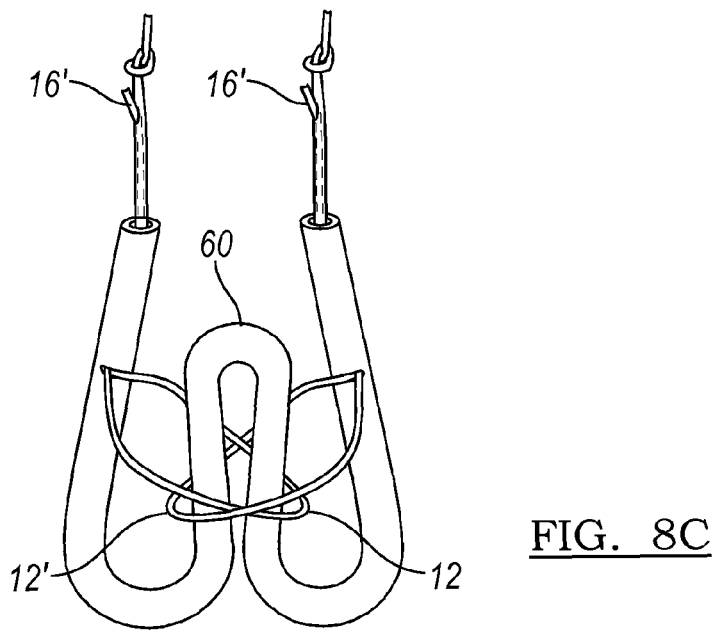
Figure 8D:
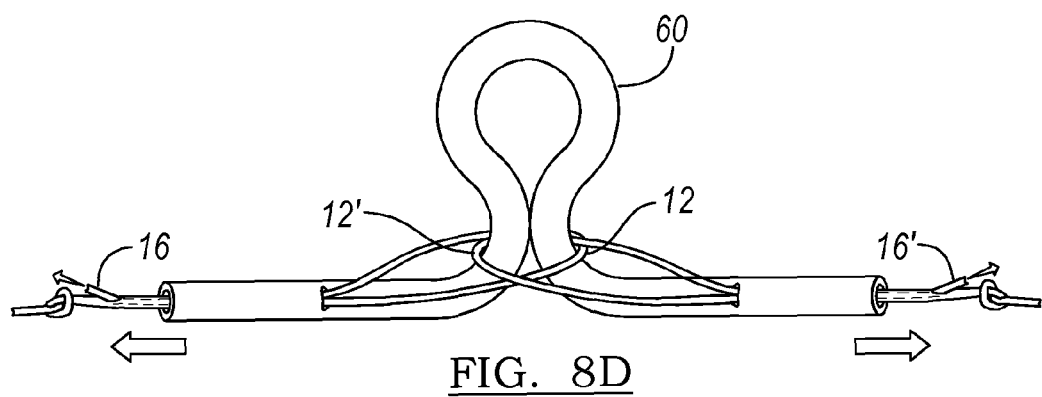

Continuing the assembly illustration at FIG. 8B, a bend 60 of the tubular flexible member is passed through the two adjustable loops 12 and 12'. When completely advanced, the bend 60 is trapped between the interlaced adjustable loops 12 and 12'. In this embodiment, the bend 60 serves as the locking member 40 and upon advancing the adjusting arms 16 and 16', the adjustable loops 12 and 12' compress about the bend 60 and thereby frictionally lock the assembly. It is understood that the additional locking member 40 such as the cylinder or bar 43 of FIG. 6C can also be used in the assembly to prevent slippage. In this embodiment, the adjustable loops 12 and 12' can be placed in the tissue 100 and also, the tubular flexible member 46 can be placed in the tissue 100.

Figure 9A:
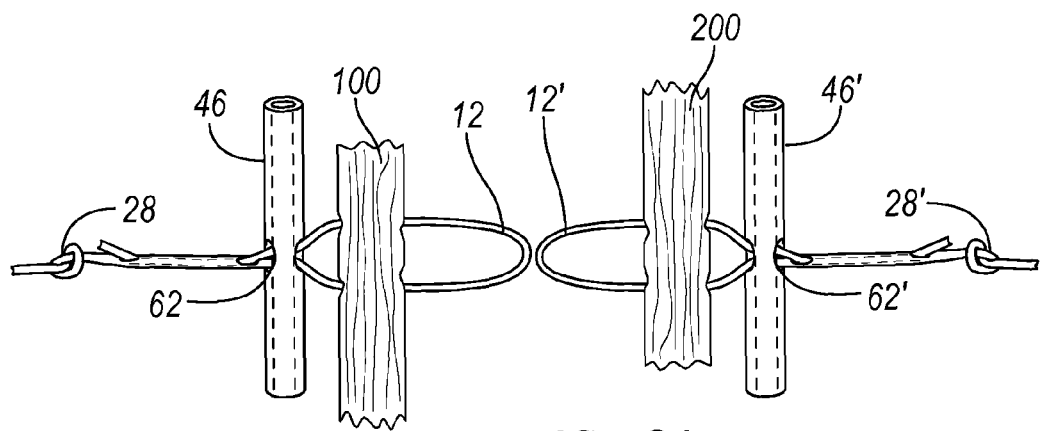
FIG. 9A-9C depict multiple tubular flexible member pathway constructs according to various embodiments.
Figures 9B, 9C:
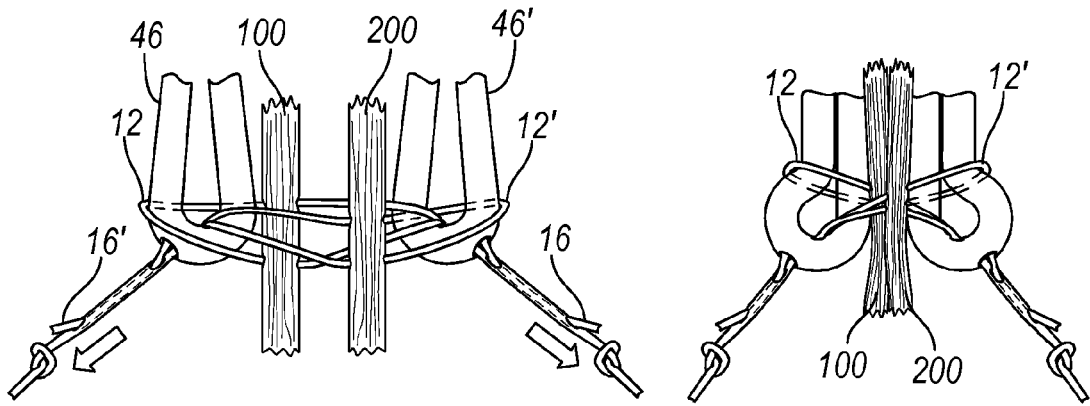

Turning to FIGS. 9A-9C, in a third embodiment of this grouping, a plurality of tubular flexible members 46 and 46' can be used to provide the assembly. Transverse openings 62 and 62' are placed in the respective tubular flexible members 46 and 46'. The adjustable loops 12 and 12' are passed through the respective transverse openings 62 and 62' as shown in FIG. 8A. The adjustable loops 12 and 12' can be passed through the first and second tissue 100 and 200 as detailed above.

The tubular flexible members 46 and 46' are then folded and disposed in the adjustable loop 12' and 12 of the opposing flexible member 46 and 46'. This causes the adjustable loops 12 and 12' to become interlaced. Upon engaging the adjusting arms 16 and 16' in the direction of the arrow, the adjustable loops 12 and 12' compress about the tubular flexible members 46 and 46' to frictionally secure the construct. Similar to the embodiment of FIGS. 7A-7D, regions of the tubular flexible members 46 and 46' serve as both the pathway construct and as the locking member. The tubular flexible members 46 and 46' and/or the adjustable loops 12 and 12' can be used to secure the tissue.

Figure 10A:
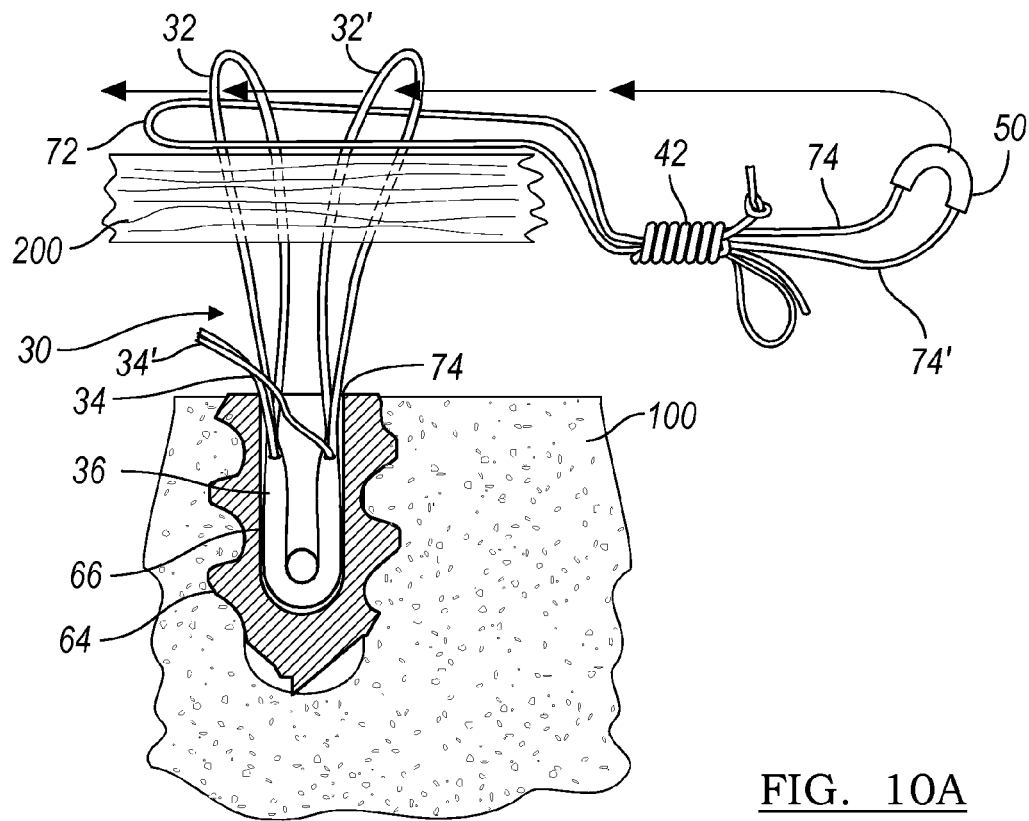
FIGS. 10A-10C depict an elbow shaped flexible member pathway according to various embodiments.
Figure 10B:
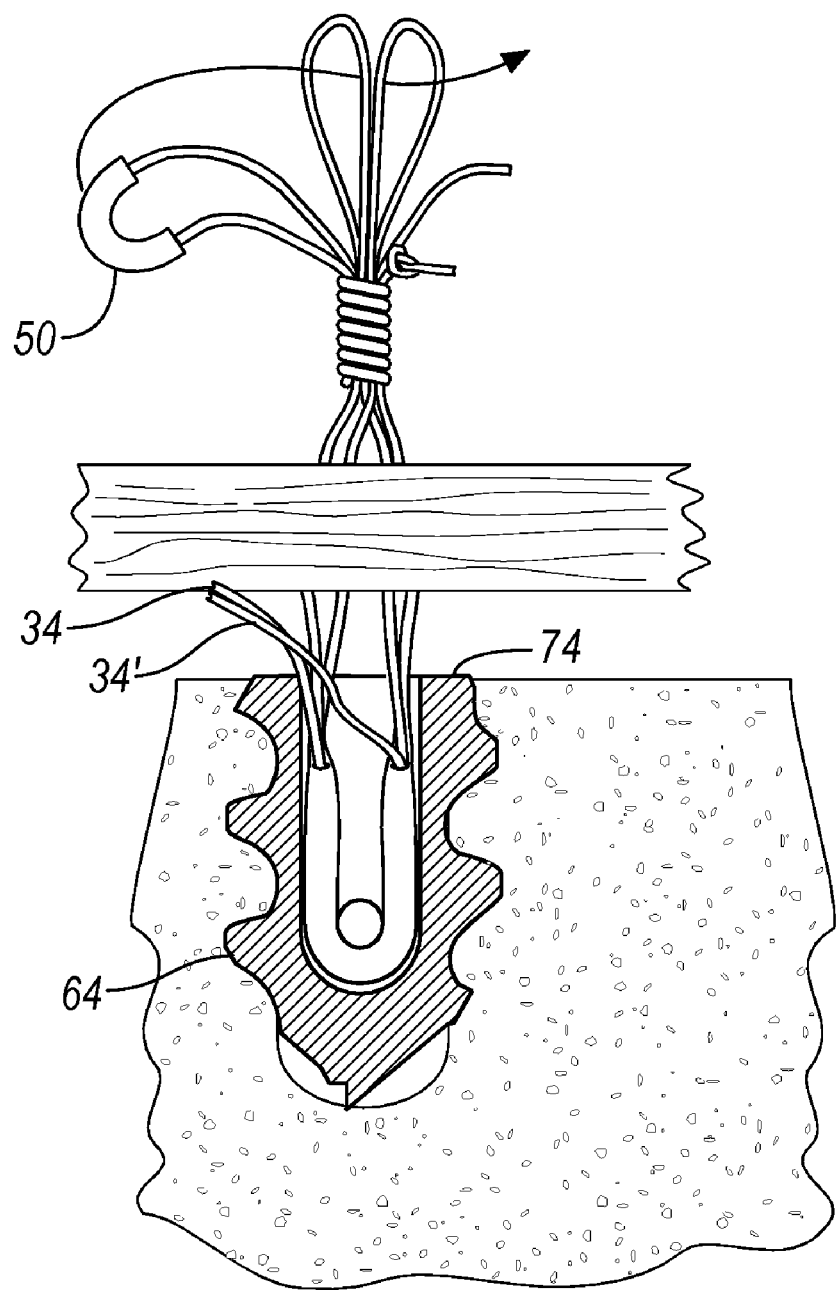
Figure 10C:
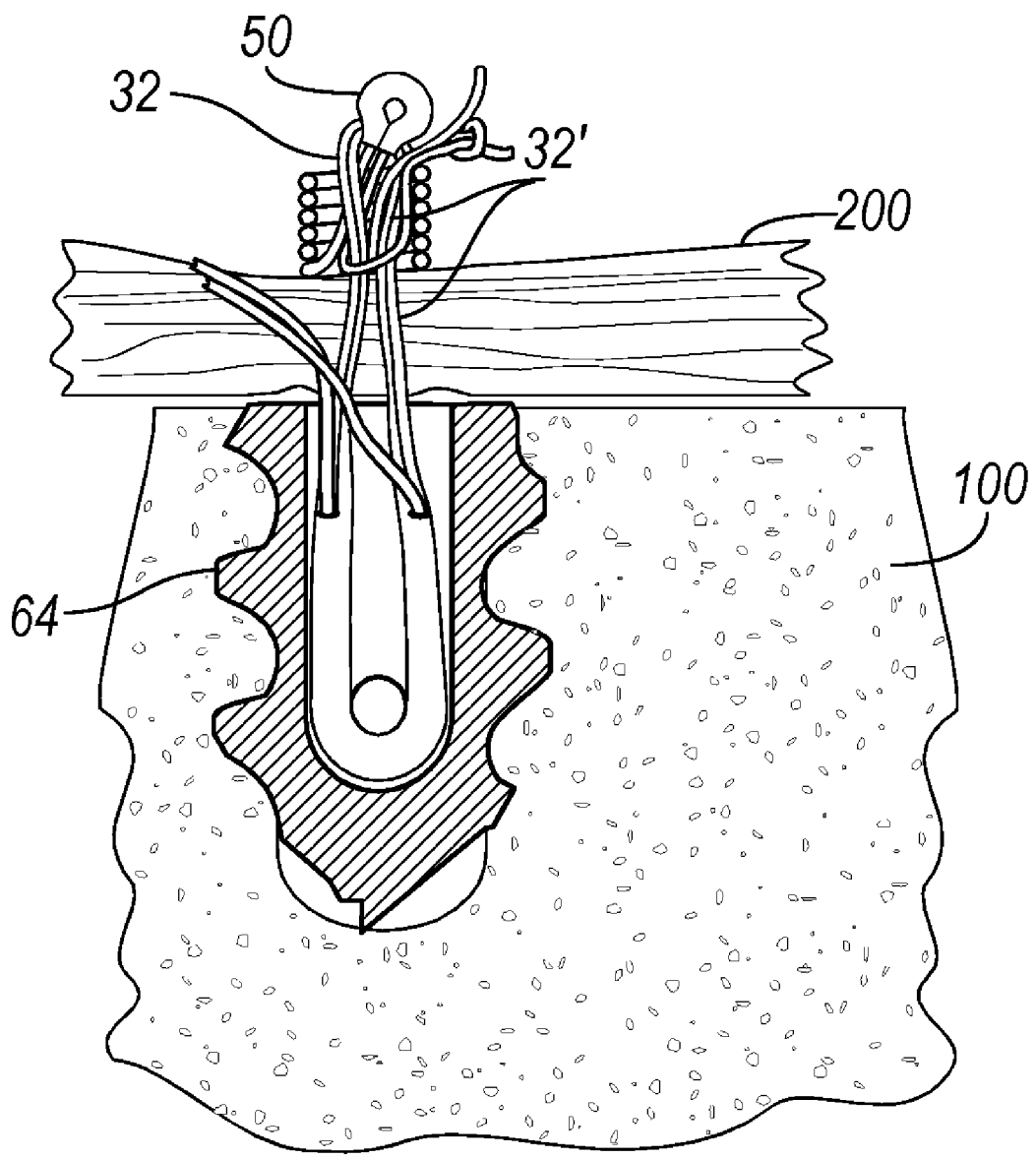

In a fourth embodiment of this grouping as shown in FIGS. 6A and 10A-10C, which is depicted with the flexible member 30, an elbow 50 locking member is employed and a suture anchor 64 serves as the pathway construct. As best shown in FIGS. 10A and 10C, this embodiment can be used to fix bone as the first tissue 100 via the suture anchor 64 and cartilage or a tendon as the second tissue 200 via the adjustable loops 32 and 32'. It is understood that the teachings are not limited to suture anchors but also include a button, a clip, or another suture-retaining device. The various suture anchors detailed herein can be made of any biocompatible material including, but not limited to, a metal, such as titanium, stainless steel, or alloys of cobalt, chromium, etc., or a polymer such as polyetheretherketone (PEEK) or polymers and copolymers of lactic and glycolic acid.

In use, the passage 36 of the flexible construct 30 is passed into a bore 66 defined by the interior of the anchor 64. The flexible construct can be passed through the interior of the anchor 64 using a guide wire or by hand. The anchor 64 is then placed into the bone first tissue 100, such as through a pre-drilled hole in the boney first tissue 100. It is also understood that a self-tapping anchor or other fastener can be used to provide the pathway construct in the boney first tissue 100.

Next, the adjustable loops 32 and 32' are passed through the tissue as detailed above. Subsequently, the elbow 50 locking member is disposed at the end of a Duncan loop 68 to create an assembly 70. The assembly is then formed by taking a length of a flexible material and passing it through the elbow 50 such that at least a portion of the flexible material extends from both sides of the elbow 50 to form arms 74 and 74'. The arm 74 is folded and repeatedly wrapped around arm 74' to provide a coil of flexible material, as was illustrated in FIGS. 7B-7D. The Duncan loop 68 can be secured with a knot or using one of the locking members of FIGS. 6A-6C.

Next, a summit 72 region of the assembly 66 is passed over the two loops 32 and 32' which extend from anchor 64. The flexible material is advanced to reduce the length of the summit 72 region, and the elbow 50 is passed through the loops 32 and 32' following the path as indicated by the arrows in FIG. 10A. Upon engaging the adjusting arms 34 and 34', the elbow 50 is drawn down towards a proximal end 74 of the anchor 64 such that the elbow 50 locking member faces or abuts the proximal end 74. The placement of the elbow 50 at the proximal end 74 fixes the flexible member 30 in the pathway construct of the anchor 64. In various embodiments, the elbow 50 can be used in conjunction with or replaced with a large knot in the assembly. Additional examples employing a suture anchor pathway construct are detailed later herein.

Referring to FIGS. 11A-11H, in the next group of embodiments, the present teachings also provide methods of attaching a first boney tissue 100 using a fastener 92 to a second soft tissue 200 using the flexible construct 10. The fastener 92 includes a fastener body 94 which extends between a proximal end 96 and a distal end 98, an axially extending interior bore 102, and at least one side bore 104 which is generally perpendicular to the interior bore 102. In various embodiments, the fastener 92 includes a plurality of side bores 104. In various embodiments, the axially extending bore 102 can have a proximal end opening which is mated to receive a tool, such as a driver for inserting the anchor, as are well known in the art.

Figure 11A:
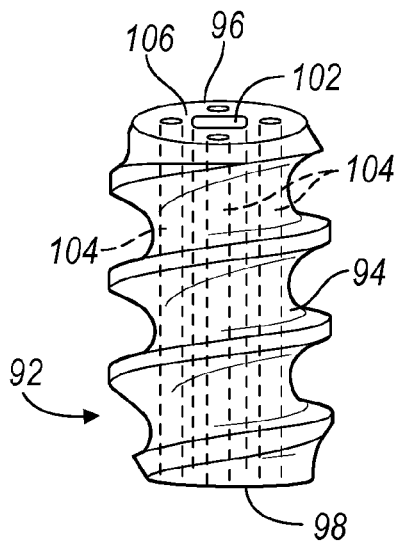
FIGS. 11A-11H depict a surgical technique using multiple flexible constructs according to various embodiments.
Figure 11B:
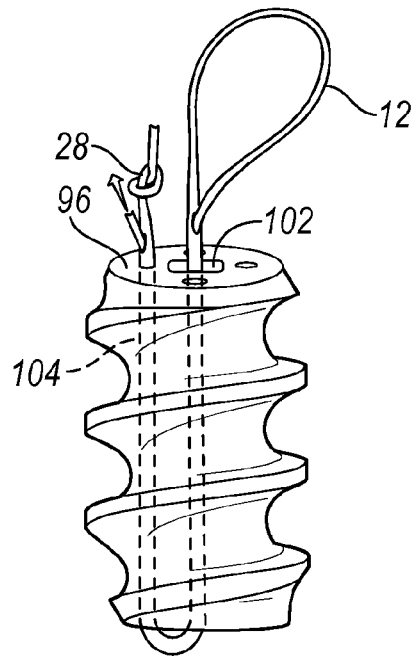
Figure 11C:
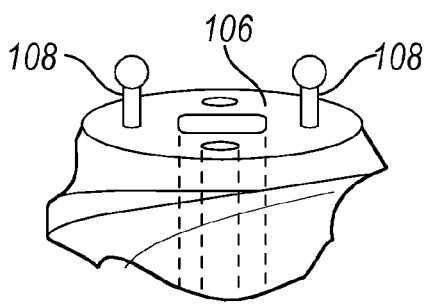
Figure 11D:
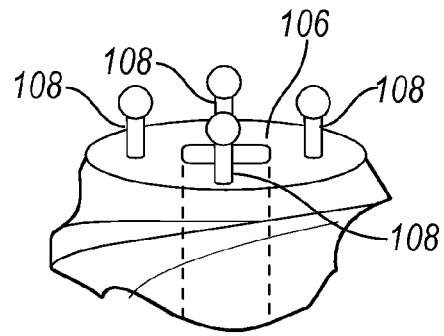
Figure 11E:
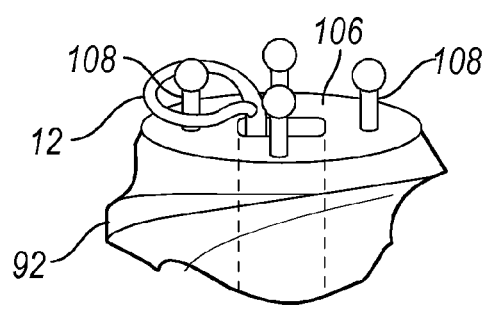

At the proximal end 96 of the fastener 92, is a receiving surface 106 used to receive a region of the flexible construct 10. As depicted in FIG. 12A, the receiving surface can be a flat surface which is flush with the receiving surface 106. As shown in FIGS. 11C-11E, the receiving surface 106 can also include various combinations of posts 108 designed to hold the adjustable loop 12 region of the flexible construct 10.

In use, the flexible construct 10 is disposed downwardly into the side bore 104 such that the restriction element 28 faces or abuts a flat or recessed region of the receiving surface 106 which is defined by the region adjacent to the opening for the side bore 104. The restriction element 28 is sized such that it is too large to pass through the side bore 104. The adjustable loop region 12 is then passed upwardly towards the proximal end 96 of the fastener through the interior bore 102 such that the adjustable loop 12 extends from the proximal end 96 of the fastener and is free for suturing of the soft tissue 100. After securing the adjustable loop 12 to the soft tissue 100, the adjusting arm 16 of the flexible construct 10 is engaged to cause reduction of the adjustable loop 12. The posts 108 at the proximal end 96 of the fastener can be used to retain the adjustable loop 12, as shown in FIG. 11 E.

Figure 11F:
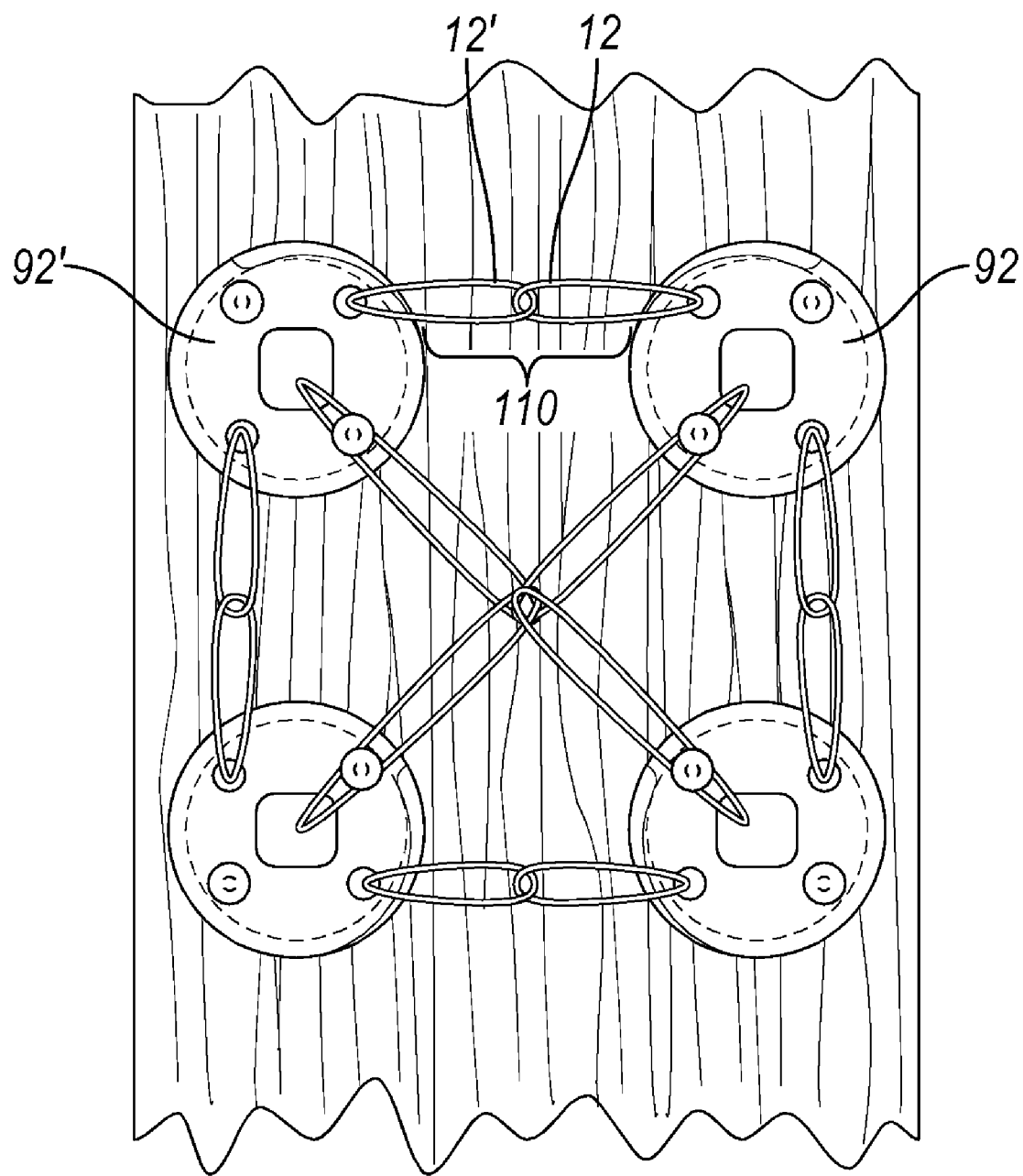
Figure 11G:
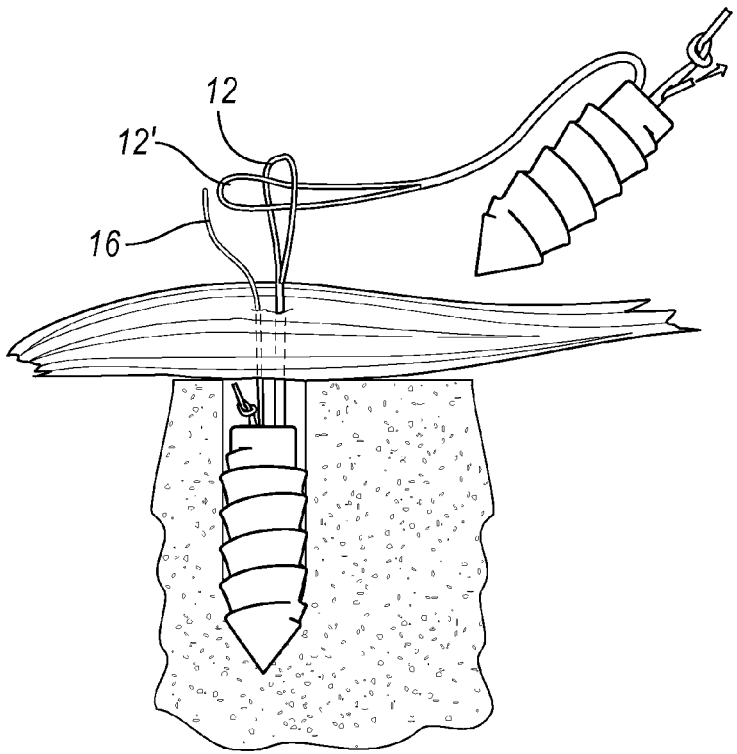
Figure 11H:
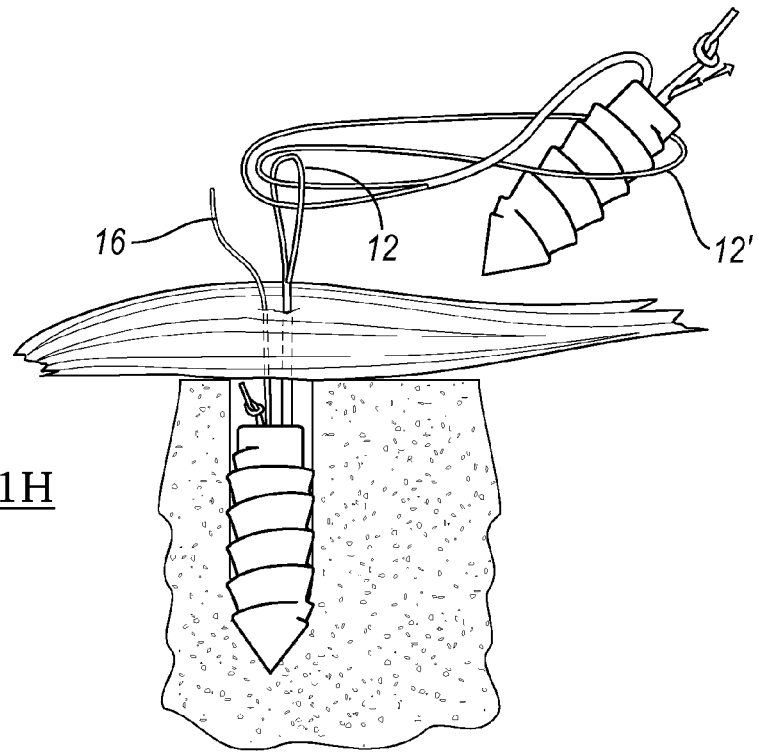

Turning to multiple fastener embodiment of FIG. 11F, a plurality of fasteners 92 and flexible constructs 10 are connected to form an interlaced web or bridge 110 of adjustable loops 12. As shown in FIGS. 11G and 11H, the fastener 92 is first placed in the boney first tissue 100 and has the adjustable loop 12 extending from the distal end of the fastener 92. A second fastener 92' having an adjustable loop 12' thereon is then passed through the adjustable loop 12. The adjustable loop 12' is then wrapped back around the fastener 92' to interlace the adjustable loops 12 and 12'. This process is repeated until the desired number of fasteners is placed at the site in need of tissue repair.

The pattern of the flexible constructs and the placement of the adjustable loops 12 can be varied as needed by the user after evaluating the soft tissue defect to provide a specialized retention and securing of the soft tissue 100. The adjustable loops 12 can be reduced in size using the respective adjusting arms 16 to retain the fastener 92 proximal end 94 in abutment with the soft tissue 200 or to reduce the distance between the anchor and the first tissue.

To start, a first fastener 92 is inserted into a pre-drilled hole in the bone and the first adjustable loop 12 is on top of the tissue. A second fastener 92' is then passed through the first adjustable loop 12 and folded back into the second adjustable loop 12' to interlace the adjustable loops 12 and 12'. The second fastener 92' is then secured through the tissue 100 and into the bone. The first adjusting arm 16 is then engaged to cause the respective loops to reduce in size and form a link or bridge 110 of interlaced adjustable loops 12 and 12' between the first fastener 92 and the second fastener 92'. The interlacing and sequential tightening is continued until the desired numbers of fasteners are placed at the defect. After the adjusting arms 16, 16' are engaged to the correct distance to reduce the respective adjustable loops and provide the appropriate amount of tissue compression and securing at the defect site, the adjusting arms 16 and 16' can be optionally cut. There is no need for the surgeon to tie a knot as the interlaced and compressed loops provide the tissue fixation. As illustrated, each fastener 92 can provide a plurality of connections.

Turning to FIGS. 14A-14D, the fastener 92 can further include a plate portion 112. The plate portion 112 includes a tip 114 and a panel 116 extending from the tip 114. The panel 116 further includes a post 118 and defines at least one suture receiving openings 120. In various embodiments, the panel includes a plurality of suture receiving openings to accommodate multiple flexible constructs 10. The suture receiving openings 120 can independently be offset from the longitudinal axis of the plate portion 112 or can be centered therewith.

Figure 14A:
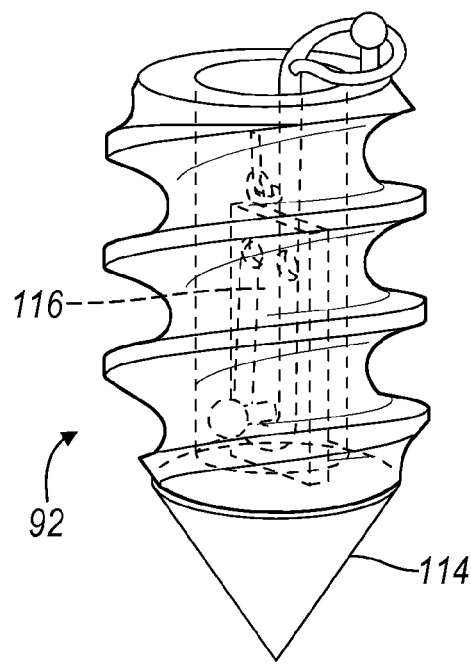
FIGS. 14A-14D depict a surgical method employing the folded tubular flexible member pathway construct according to various embodiments.
Figure 14B:
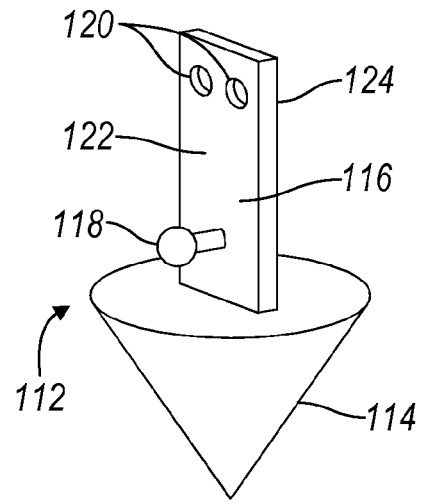
Figure 14C:
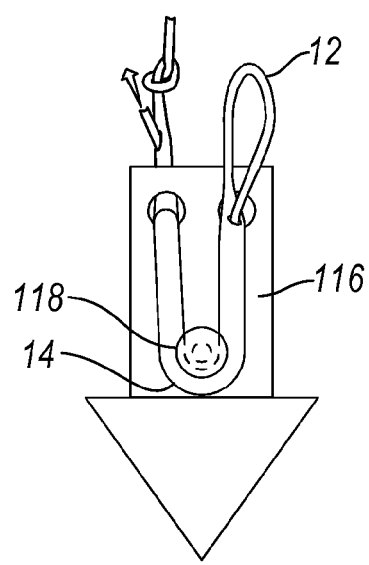
Figure 14D:
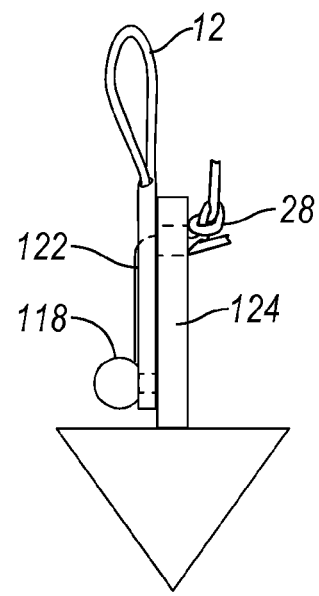

In use, the adjustable member 12 is secured to the plate tip 112 by passing the adjustable loop 12 through the suture receiving opening 120 such that the adjustable loop 12 is on a first side 122 of the panel 116 and the securing element is on the second side 124 of the panel 116. The restriction element 28 is sized to be larger than the suture receiving opening such that the flexible construct does not slip off of the panel 116. The passage 14 is then placed on the post 118. The placement of the adjustable loop 12 and the restriction element 28 are best depicted in FIGS. 14C and 14D, respectively. The panel 116 having the flexible construct 10 thereon can be used as detailed above in connection with a single fastener or multiple fastener system.

In still further embodiments, a locking member can be passed through the two adjustable loops when they are used in an interlaced or bridge formation. The method is substantially the same as the immediately above-described technique. Instead of interlacing the adjustable loops 12 with each other, the adjustable loops 12 are placed on a self-contained locking member 140 as depicted in FIGS. 13A-13C and 12A-12C. The adjustable loops can be placed on the self-contained locking member 140 prior to or after suturing the soft tissue.

To prepare the self-contained locking member 140, an adjustable loop 12 of a flexible construct is reduced by engaging the adjusting arm 16. As shown in FIG. 12B, the I-shaped locking member 41 is used as a temporary place holder and inserted into the reduced adjustable loop 12 to maintain the integrity of the adjustable loop 12 and prevent collapse of the system. Next, the adjustable loops 12', 12", and 12''' used for the suturing are then disposed along the passage length 14 of the flexible construct 10 as shown in FIG. 12B.

The restriction element 28 is advanced in the direction of the arrow and is passed through the small opening of the adjustable loop 12. If a temporary locking member 41 place holder was employed, it can be optionally removed. The adjusting arm 16 can be further engaged or tightened to constrict the restriction element in the adjustable loop 12.

It is understood that connecting the adjustable loops 12 can be performed prior to or after suturing the tissue. The self-contained locking member 140 allows for slack to be placed in the system between the connection of the various adjustable loops 12', 12", and 12'''.

Figure 13A:
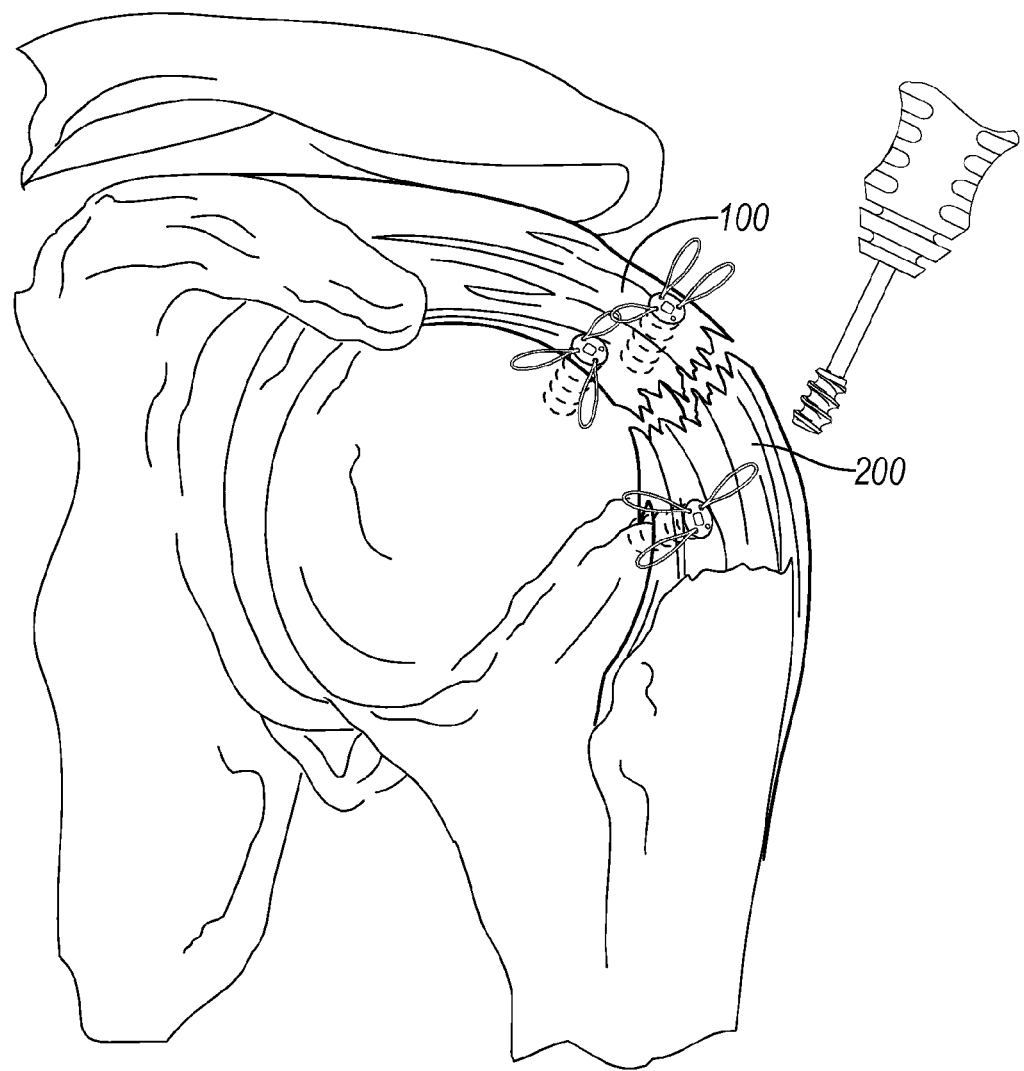
FIGS. 13A-13C depict a folded tubular flexible member pathway construct according to various embodiments.
Figure 13B:
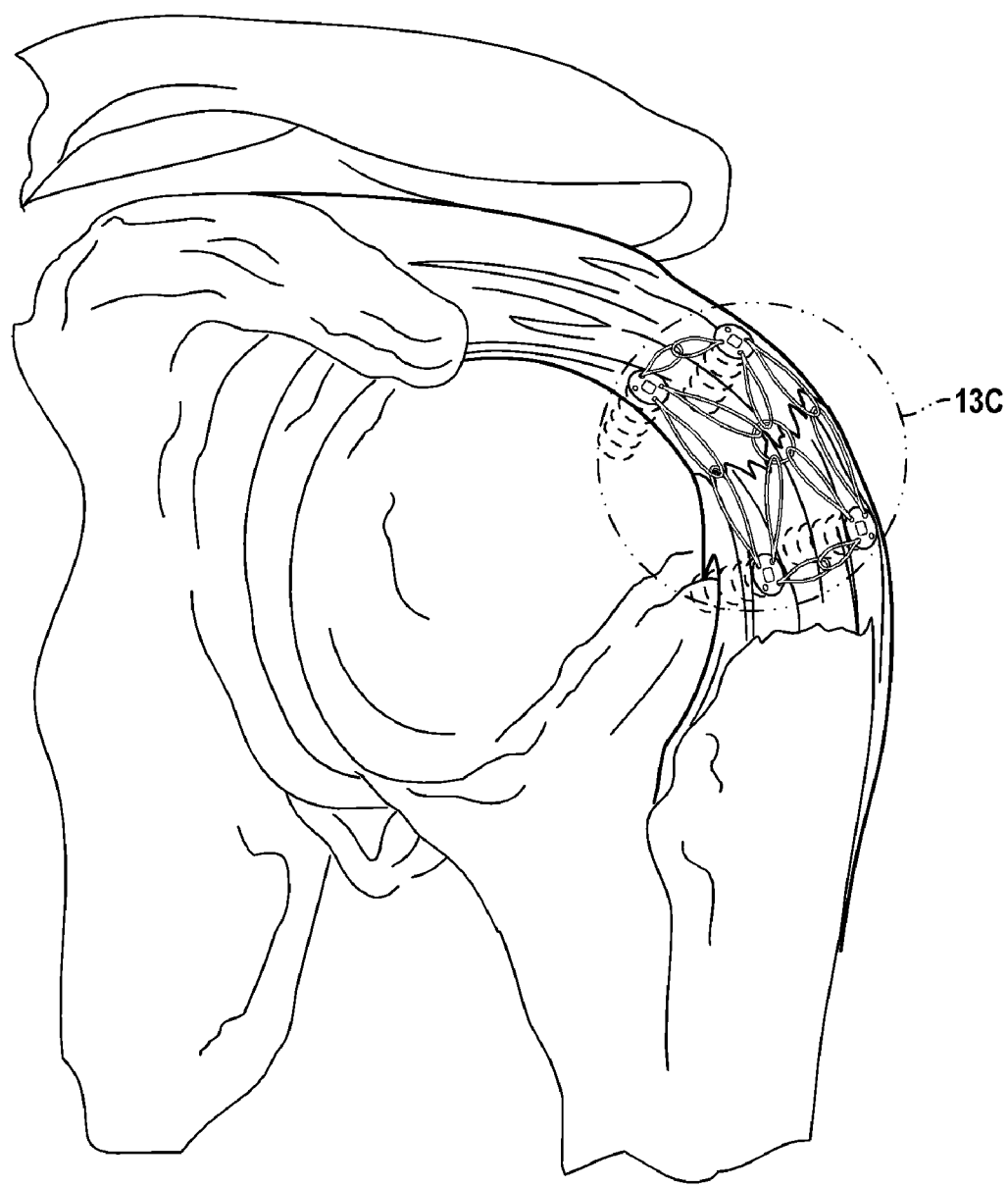
Figure 13C:
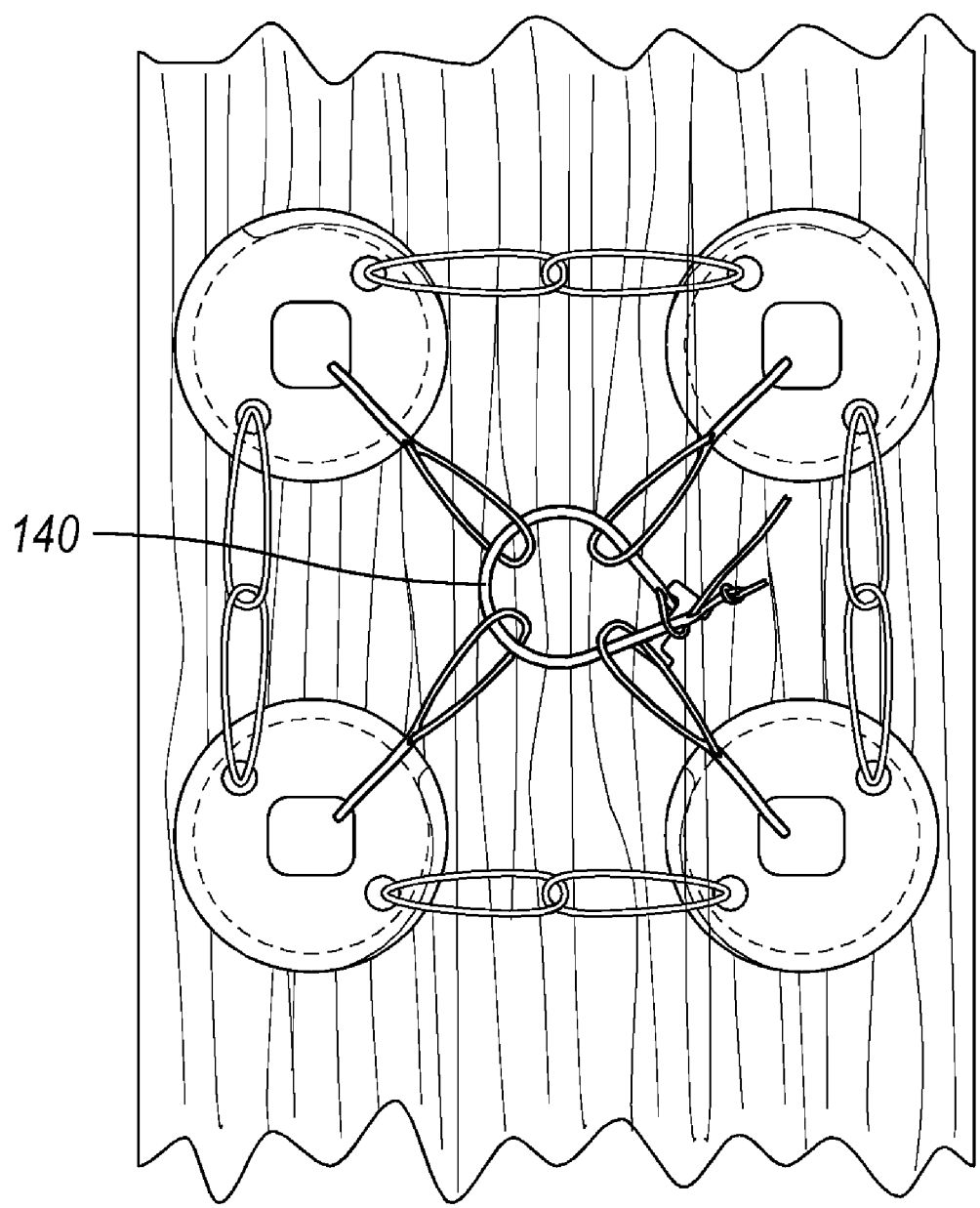

As illustrated in FIGS. 13A-13C, the self-contained locking member 140 can be strategically placed between various fasteners 92 for use in lateral row repair of a rotator cuff having torn tissue segments 150 and 152. Similar to the multi-fastener placement detailed above with respect to FIG. 11F, several fasteners 92 can be placed medially and laterally to the torn rotator cuff. The adjustable loops 12 extending from the respective fasteners can be interlaced using a combination of the interlace technique depicted in FIGS. 11G and 11H, can be interlaced by connection to the self-contained locking member 14, or a combination thereof. As shown, at least fastener 92 or row of fasteners is placed laterally with respect to the other fastener or fasteners. The self-contained locking member 140 can be placed along the length of a medial lateral row repair to facilitate increasing the footprint of the repaired tissue as shown in FIGS. 13B and 13C. It is understood that all of the multiple fastener placements disclosed herein can include the second or any subsequent fastener being placed lateral, medial, anterior, or posterior with respect to the first fastener or any other fastener.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A method of attaching a first tissue to a second tissue at a site, comprising:
   positioning a fastener in the first tissue, the fastener carrying a flexible member construct extending therefrom, the flexible member construct including a flexible member having a body defining a passage portion and first and second ends, the first and second ends extending through the passage portion to form first and second adjustable loops relative to the passage portion;
   passing the first and second adjustable loops through the second tissue;
   passing a locking member through the first and second adjustable loops; and
   reducing a size of the first and second adjustable loops about the locking member such that the first and second adjustable loops are retained relative to the second tissue and the second tissue is fixed to the first tissue.

2. The method according to claim 1, wherein positioning the fastener in the first tissue comprises passing the flexible member construct through an internal bore defined by the fastener such that the first and second adjustable loops extend from the internal bore.

3. The method according to claim 2, further comprising positioning the passage portion within the internal bore.

4. The method according to claim 1, wherein reducing the size of the first and second adjustable loops about the locking member includes engaging and tensioning first and second adjusting arms defined by the flexible member of the flexible member construct.

5. The method according to claim 4, further comprising engaging and tensioning the first and second adjusting arms to draw the second tissue into engagement with the first tissue, the first and second adjusting arms extending from the passage portion of the flexible member construct.

6. The method according to claim 1, wherein passing the locking member through the first and second adjustable loops includes passing the locking member through the first and second adjustable loops adjacent a surface of the second tissue facing a direction opposite the first tissue.

7. The method according to claim 1, wherein passing the locking member through the first and second adjustable loops includes passing an elbow slidably coupled to a flexible member loop through the first and second adjustable loops.

8. The method according to claim 1, wherein passing the locking member through the first and second adjustable loops further comprises forming a locking member assembly including:
   forming a pathway construct as a coil using at least a second flexible member so as to position third and fourth adjustable loops relative to the coil; and
   passing a portion of the locking member assembly through the first and second adjustable loops.

9. The method according to claim 8, wherein passing the portion of the locking member assembly through the first and second adjustable loops includes passing the third adjustable loop through the first and second adjustable loops.

10. The method according to claim 9, wherein passing the third adjustable loop through the first and second adjustable loops includes passing an elbow slidably coupled to the third adjustable loop through the first and second adjustable loops.

11. The method according to claim 10, further comprising:
    positioning the fourth adjustable loop around respective portions of the first and second adjustable loops extending through the second tissue; and
    reducing a size of the fourth adjustable loop so as to constrict the fourth adjustable loop around the respective portions of the first and second adjustable loops.

12. The method according to claim 11, wherein reducing the size of the fourth adjustable loop includes reducing the size of the fourth adjustable loop after passing the third adjustable loop though the first and second adjustable loops.

13. The method according to claim 11, wherein reducing a size of the first and second adjustable loops about the locking member includes reducing a size of the first and second adjustable loops about the elbow to retain the first and second adjustable loops relative to the second tissue and draw the elbow and second tissue toward the first tissue.

14. The method according to claim 1, wherein positioning the fastener in the first tissue includes positioning the fastener in bone.

15. A method of attaching a first tissue to a second tissue at a site, comprising:
    attaching an adjustable flexible member construct to a fastener, the flexible member construct including a flexible member having a body defining a passage portion and first and second ends, the first and second ends extending through the passage portion to form first and second adjustable loops relative to the passage portion;
    positioning the fastener in the first tissue;
    attaching the first and second adjustable loops to the second tissue;
    passing a portion of a locking member assembly through the first and second adjustable loops; and
    reducing a size of the first and second adjustable loops about the portion of the locking member assembly such that the first and second adjustable loops are retained relative to the second tissue and the second tissue is fixed to the first tissue.

16. The method according to claim 15, further comprising forming the locking member assembly including:
    forming a pathway construct as a coil using at least a second flexible member so as to position third and fourth adjustable loops relative to the coil; and
    slidably coupling an elbow to the third adjustable loop;
    wherein passing a portion of the locking member assembly through the first and second adjustable loops includes passing the elbow and a portion of the third adjustable loop through the first and second adjustable loops.

17. The method according to claim 16, further comprising:
    passing the first and second adjustable loops through the second tissue;
    positioning the fourth adjustable loop around a portion of the first and second adjustable loops extending through the second tissue; and
    reducing a size of the fourth adjustable loop so as to constrict the fourth adjustable loop about the first and second adjustable loops before passing the elbow through the first and second adjustable loops.

18. The method according to claim 17, wherein reducing the size of the first and second adjustable loops about the locking member assembly includes tensioning first and second adjusting arms defined by the flexible member of the flexible member construct to reduce the size of the first and second adjustable loops about the elbow and draw the second tissue toward the first tissue.

19. The method according to claim 16, wherein forming the pathway construct as a coil using at least a second flexible member so as to position third and fourth adjustable loops relative to the coil includes:
    providing second and third adjustable flexible member constructs each having the respective third and fourth adjustable loops and including respective third and fourth adjusting arms; and
    forming the pathway construct as the coil about the second and third adjustable flexible member constructs by wrapping one of the third and fourth adjusting arms around passage portions of the second and third adjustable flexible member constructs.

20. The method according to claim 15, wherein positioning the fastener in the first tissue includes positioning the fastener in bone, and wherein attaching the first and second adjustable loops to the second tissue includes positioning the first and second adjustable loops through soft tissue.

21. A method of attaching a first tissue to a second tissue at a site, comprising:
    positioning a fastener in the first tissue, the fastener carrying a flexible member construct extending from an internal bore, the flexible member construct including a flexible member having a body defining a passage portion and first and second ends, the first and second ends extending through the passage portion to form first and second adjustable loops extending from the passage portion;
    passing the first and second adjustable loops through the second tissue;

passing a third adjustable flexible member loop of a locking member assembly around a portion of the first and second adjustable loops extending through the second tissue;

reducing a size of the third adjustable loop relative to the first and second adjustable loops;

passing a fourth flexible member loop of the locking member assembly through the first and second adjustable loops, the fourth flexible member loop including a locking member coupled thereto; and reducing a size of the first and second adjustable loops about the locking member and fourth adjustable loop such that the first and second adjustable loops are retained relative to the locking member and the second tissue is fixed to the first tissue.

22. The method according to claim 21, wherein reducing the size of the third adjustable loop relative to the first and second adjustable loops includes reducing the size of the third adjustable loop relative to a flexible member coil formed relative to the third and fourth adjustable loops.

23. The method according to claim 21, wherein reducing the size of the third adjustable loop relative to the first and second adjustable loops includes constricting the third adjustable loop around the portion of the first and second adjustable loops extending through the second tissue.

24. The method according to claim 23, wherein passing the fourth flexible member loop of the locking member assembly through the first and second adjustable loops includes passing an elbow slidably coupled to the fourth flexible member loop and a portion of the fourth flexible member loop through the first and second adjustable loops.

25. The method according to claim 24, wherein reducing the size of the first and second adjustable loops about the locking member and fourth flexible member loop includes engaging first and second adjusting arms defined by the flexible member of the flexible member construct to reduce the size of the first and second adjustable loops about the elbow and relative to the third adjustable loop of the locking member assembly.

* * * * *